(12) United States Patent
Hashimoto et al.

(10) Patent No.: US 9,415,068 B2
(45) Date of Patent: Aug. 16, 2016

(54) METHOD FOR INHIBITING DENTINAL HYPERSENSITIVITY

(71) Applicant: KURARAY NORITAKE DENTAL INC., Kurashiki-shi (JP)

(72) Inventors: Tadashi Hashimoto, Kurashiki (JP); Mariko Sugiura, Kurashiki (JP); Shumei Ishihara, Kurashiki (JP); Mitsunobu Kawashima, Kurashiki (JP); Koichi Okada, Tokyo (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 225 days.

(21) Appl. No.: 13/896,994

(22) Filed: May 17, 2013

(65) Prior Publication Data

US 2013/0251767 A1  Sep. 26, 2013

Related U.S. Application Data

(62) Division of application No. 13/259,681, filed as application No. PCT/JP2010/055379 on Mar. 26, 2010, now abandoned.

(30) Foreign Application Priority Data

Mar. 30, 2009 (JP) ................. 2009-082957

(51) Int. Cl.
| | | |
|---|---|---|
| *A61K 47/02* | (2006.01) | |
| *A61Q 11/00* | (2006.01) | |
| *A61K 47/04* | (2006.01) | |
| *A61P 1/02* | (2006.01) | |
| *A61K 6/033* | (2006.01) | |
| *A61P 25/02* | (2006.01) | |
| *A61K 33/16* | (2006.01) | |
| *A61K 8/24* | (2006.01) | |
| *A61K 33/42* | (2006.01) | |
| *A61K 6/00* | (2006.01) | |
| *A61K 8/02* | (2006.01) | |
| *A61K 45/06* | (2006.01) | |

(52) U.S. Cl.
CPC ............. *A61K 33/42* (2013.01); *A61K 6/0017* (2013.01); *A61K 6/033* (2013.01); *A61K 8/0241* (2013.01); *A61K 8/24* (2013.01); *A61K 33/16* (2013.01); *A61K 45/06* (2013.01); *A61Q 11/00* (2013.01); *A61K 2800/412* (2013.01)

(58) Field of Classification Search
CPC ..... A61K 6/0017; A61K 8/004; A61K 47/02; A61K 33/42; A61K 33/06; A61K 8/044; A61K 8/0241; A61K 8/24; A61K 6/00; A61K 6/0008; A61K 6/0082; A61K 33/16; A61Q 11/00

See application file for complete search history.

(56) References Cited

U.S. PATENT DOCUMENTS

| | | | |
|---|---|---|---|
| 5,522,893 A | 6/1996 | Chow et al. | |
| 5,833,954 A * | 11/1998 | Chow et al. | ............... 424/49 |
| 6,733,582 B1 | 5/2004 | Bohner et al. | |
| 2005/0020720 A1 | 1/2005 | Dickens et al. | |
| 2005/0260278 A1 | 11/2005 | Constantz et al. | |
| 2006/0011100 A1 | 1/2006 | Lin et al. | |
| 2007/0092856 A1 | 4/2007 | Chow et al. | |
| 2010/0236449 A1 | 9/2010 | Hashimoto et al. | |
| 2010/0323022 A1 | 12/2010 | Hashimoto et al. | |

FOREIGN PATENT DOCUMENTS

| | | |
|---|---|---|
| CN | 1233964 | 11/1999 |
| JP | 61 167607 | 7/1986 |
| JP | 01 163127 | 6/1989 |
| JP | 02 258602 | 10/1990 |
| JP | 05 255029 | 10/1993 |
| JP | 3017536 | 3/2000 |
| JP | 2001-348212 | 12/2001 |
| JP | 2003 516190 | 5/2003 |
| JP | 2007-190226 | 8/2007 |
| JP | 2007 197329 | 8/2007 |
| JP | 2007 524635 | 8/2007 |
| JP | 2007 537844 | 12/2007 |
| JP | 2009 512713 | 3/2009 |
| JP | 2009 195452 | 9/2009 |
| WO | 98/07448 | 2/1998 |
| WO | WO 2007083601 A1 | 7/2007 |
| WO | 2009 099136 | 8/2009 |

OTHER PUBLICATIONS

Cherng et al., Journal of Biomedical Materials Research Part B: Applied Biomaterials, Aug;78(2):291-5 (2006).*

International Search Report Issued May 11, 2010 in PCT/JP10/055379 Filed Mar. 26, 2010.

(Continued)

*Primary Examiner* — Kortney L Klinkel
*Assistant Examiner* — Lisbeth C Robinson
(74) *Attorney, Agent, or Firm* — Oblon, McClelland, Maier & Neustadt, L.L.P.

(57) ABSTRACT

A method for inhibiting dentinal hypersensitivity by applying a dentinal hypersensitivity inhibitor on a dentin surface. The dentinal hypersensitivity inhibitor contains at least one tetracalcium phosphate particle, an alkali metal salt of phosphoric acid, and at least one acidic calcium phosphate particle. The tetracalcium phosphate particle has an average particle diameter of 0.5 to 40 µm. The dentinal hypersensitivity inhibitor contains a blended amount of the tetracalcium phosphate particle of 5 to 55 parts by weight relative to 100 parts by weight of a whole amount of the dentinal hypersensitivity inhibitor and a blended amount of the alkali metal salt of phosphoric acid of 1 to 100 parts by weight relative to 100 parts by weight of the tetracalcium phosphate particle.

9 Claims, 2 Drawing Sheets

(56) References Cited

OTHER PUBLICATIONS

Extended Search Report issued Aug. 30, 2012 in European Application No. 10758572.1.
E. F. Burguera, et al., "A water setting tetracalcium phosphate-dicalcium phosphate dihydrate cement", Journal of Biomedical Materials Research, vol. 71A, No. 2, Nov. 1, 2004, XP002681995, pp. 275-282.
Hashimoto et al. JPO machine translation of JP 2007-190226 A (2007).
Office Action in Chinese Patent Application 201080024026.X, filed Mar. 26, 2010 (with English Translation).

* cited by examiner 4  5

METHOD FOR INHIBITING DENTINAL HYPERSENSITIVITY

CROSS REFERENCE TO RELATED APPLICATIONS

The present application is a divisional of U.S. patent application Ser. No. 13/259,681, filed on Sep. 30, 2011, the text of which is incorporated by reference, which is a 35 U.S.C. §371 national stage patent application of International patent application PCT/JP2010/55379, filed on Mar. 26, 2010, the text of which is incorporated by reference, which claims priority to Japanese patent application JP 2009-082957, filed on Mar. 30, 2009, the text of which is incorporated by reference.

TECHNICAL FIELD

The present invention relates to dentin mineralizing agents for mineralizing a dentin surface and a deep portion of a dentinal tubule.

BACKGROUND ART

Along with a so-called "8020 campaign" (improvement in dental health, preservation of dentin (MI: Minimal Intervention)) to try to keep 20 or more own teeth even when being 80 years old, the ratio at which many teeth remain in aged persons have rapidly increased. In association with this, however, a problem of dentin exposure due to new dental diseases (e.g., wear of teeth, alveolar bone loss caused by periodontal disease, etc.) has arisen. Exposed dentin is not good in caries resistance because unlike the enamel, tissues constituting the dentin is low in mineral concentration, and the exposed dentin may cause development of, for example, hyperesthesia when a dentinal tubule comes to be open by the action of an acid in an oral cavity. As a method of improving this, there have been known a method of coating with a polymeric material and a method of applying two materials alternately to make an inorganic salt deposit to form a physical barrier, thereby closing dentinal tubules. However, these methods have a problem that a cover is worn by a toothbrush or the like to be broken easily because only a surface or a shallow portion near openings of dentinal tubules are covered. Moreover, although being a material with high biocompatibility, there has been another problem with it that application of the material makes a plaque adhere, causing inflammation and root caries.

On the other hand, a calcium phosphate cement (hereinafter sometimes abbreviated as "CPC") in which tetracalcium phosphate (hereinafter sometimes abbreviated as "TTCP") and dicalcium phosphate anhydrous (hereinafter sometimes abbreviated as "DCPA") has been known as a calcium phosphate composition having setting property, which has been reported to be converted, within a living body and within an oral cavity, gradually into a bioabsorbable hydroxyapatite (hereinafter sometimes abbreviated as "HAp"; $Ca_{10}(PO_4)_6(OH)_2$) which can further unite with a biological hard tissue with its form maintained.

For example, Japanese Patent No. 3017536 (patent document 1) discloses that a calcium phosphate composition including tetracalcium phosphate and dicalcium phosphate anhydrous reacts in the presence of water to form hydroxyapatite. It has been reported that the thus obtained hydroxyapatite can replace bone gradually when it comes into contact with a biological hard tissue, and the aforementioned calcium phosphate composition is usable as a remineralizing agent because it possesses remineralization potential. On the other hand, it has been disclosed that an alkali metal salt of phosphoric acid, such as disodium hydrogen phosphate ($Na_2HPO_4$), is added in order to achieve rapid setting of the above-mentioned calcium phosphate composition. However, it has been neither disclosed nor suggested that an alkali metal salt of phosphoric acid is added for the purpose of improving the effect of mineralization.

JP 1-163127 A (Patent Document 2) discloses a composition for recovery from hyperesthesia comprising tetracalcium phosphate, calcium phosphate having a Ca/P molar ratio of less than 1.67, and a thickener. This reports that the composition can reduce hyperesthesia when it is applied to a hyperesthetic site of a tooth and held for a prescribed time. The reason for such remarkable reduction in hyperesthesia is believed that calcium ions or phosphate ions eluted from a kneaded mass of such a composition with water or the like diffuse and penetrate into dentinal tubules, then hydroxyapatite deposits in the dentinal tubules, so that external mechanical stimulation, thermal stimulation, and chemical stimulation are intercepted. On the other hand, it is also disclosed that other ingredients, such as hydroxyapatite, calcium fluoride, titanium oxide, calcium hydroxide, sodium phosphate, ammonium phosphate, alumina, and silica, may be added to the aforementioned composition for hyperesthesia treatment in order to adjust kneadability with water or paste viscosity. However, it has been neither disclosed nor suggested that an alkali metal salt of phosphoric acid is added for the purpose of improving the effect of mineralization.

PRIOR ART DOCUMENTS

Patent Documents

Patent document 1: Japanese Patent No. 3017536
Patent Document 2: JP 1-163127 A

DISCLOSURE OF THE INVENTION

Problems to be Solved by the Invention

The present invention was devised in order to solve the above-described problems, and the object thereof is to provide a dentin mineralizing agent by which a dense HAp is formed on a dentin surface and HAp is deposited to a deep portion of a dentinal tubule, so that it can close the dentinal tubule.

Means for Solving the Problems

The aforementioned problems are solved by providing a dentin mineralizing agent comprising tetracalcium phosphate particles (A) and an alkali metal salt of phosphoric acid (B), wherein the dentin mineralizing agent contains the tetracalcium phosphate particles (A) in an amount of 1 to 80 parts by weight relative to 100 parts by weight of the whole amount of the dentin mineralizing agent, and the blended amount of the alkali metal salt of phosphoric acid (B) relative to 100 parts by weight of the tetracalcium phosphate particles (A) is 1 to 100 parts by weight.

At this time, it is preferred that the alkali metal salt of phosphoric acid (B) is disodium hydrogen phosphate and/or sodium dihydrogen phosphate, and it is preferred that the agent further comprises acidic calcium phosphate particles (C). Preferably, the acidic calcium phosphate particles (C) are at least one member selected from the group consisting of dicalcium phosphate anhydrous [$CaHPO_4$] particles, monocalcium phosphate anhydrous [$Ca(H_2PO_4)_2$] particles, tricalcium phosphate [$Ca_3(PO_4)_2$] particles, amorphous calcium phosphate $[Ca_3(PO_4)_2 \cdot xH_2O]$ particles, calcium dihydrogen pyrophosphate $[CaH_2P_2O_7]$ particles, dicalcium phosphate dihydrate $[CaHPO_4 \cdot 2H_2O]$ particles, and monocalcium phosphate monohydrate $[Ca(H_2PO_4)_2 \cdot H_2O]$ particles, and it is preferred that the blending ratio (A/C) of the tetracalcium phosphate particles (A) to the acidic calcium phosphate particles (C) is from 40/60 to 60/40 in molar ratio. Preferably, the agent further comprises a fluorine compound (D), and it is preferred that the fluorine compound (D) is sodium fluoride. Preferably, the average particle diameter of the tetracalcium phosphate particles (A) is 0.5 to 40 µm, and it is preferred that an average particle diameter of the alkali metal salt of phosphoric acid (B) is 0.5 to 20 µm. Preferably, an average particle diameter of the acidic calcium phosphate particles (C) is 0.1 to 7 µm, and it is preferred that the agent further comprise particles (E) of 0.002 to 2 µm in average particle diameter selected from silica or metal oxides.

At this time, preferably, when a suspension is prepared by adding 0.05 g of the dentin mineralizing agent into 200 g of pure water of 25° C., a free alkali metal ion concentration of the suspension at a time of 10 minutes after the adding is 0.2 to 100 mg/L, and it is preferred that a standard deviation σ determined when an average of the free alkali metal ion concentration is expressed by d satisfies σ≤0.3d and also preferred that the alkali metal ion is a sodium ion.

At this time, it is preferred that a dentin penetration inhibition ratio achieved when one side of a 700 µm thick bovine tooth disc is treated with the dentin mineralizing agent satisfies the following formula (1):

[1−(penetrated amount of a mineralized bovine tooth disc)/(penetrated amount of an unmineralized bovine tooth disc)]×100≥70   (I).

A tooth surface-treating material comprising the dentin mineralizing agent is a preferred embodiment of the present invention, and a dentifrice comprising the dentin mineralizing agent is a preferred embodiment of the present invention. A chewing gum comprising the dentin mineralizing agent is a preferred embodiment of the present invention, a dentinal hypersensitivity inhibitor composed of the dentin mineralizing agents is a preferred embodiment of the present invention.

Another preferred embodiment of the present invention is a dentinal hypersensitivity inhibitor composed of the dentin mineralizing agent, wherein the dentinal hypersensitivity inhibitor further comprises acidic calcium phosphate particles (C), the tetracalcium phosphate particles (A) has an average particle diameter of 0.5 to 40 µm, the blended amount of the tetracalcium phosphate particles (A) relative to 100 parts by weight of the whole amount of the dentinal hypersensitivity inhibitor is 5 to 55 parts by weight, and the dentinal hypersensitivity inhibitor is a material to be used for closing dentinal tubules by rubbing a dentin surface therewith. Another preferred embodiment of the present invention is a dentinal hypersensitivity inhibitor composed of the dentin mineralizing agent, wherein when a suspension is prepared by adding 0.05 g of the dentinal hypersensitivity inhibitor into 200 g of pure water of 25° C., a free alkali metal ion concentration of the suspension at a time of 10 minutes after the adding is 0.2 to 100 mg/L. At this time, it is preferred that the agent further comprise acidic calcium phosphate particles (C).

Moreover, the aforementioned problems are solved by providing a method for producing a dentin mineralizing agent, the method comprising mixing tetracalcium phosphate particles (A), an alkali metal salt of phosphoric acid (B), and a liquid or aqueous paste comprising water as a main ingredient, wherein 1 to 100 parts by weight of the alkali metal salt of phosphoric acid (B) is blended to 100 parts by weight of the tetracalcium phosphate particles (A), and the blended amount of the tetracalcium phosphate particles (A) relative to 100 parts by weight of the whole amount of the dentin mineralizing agent is adjusted to 1 to 80 parts by weight.

At this time, preferably, a powder comprising the tetracalcium phosphate particles (A) and the alkali metal salt of phosphoric acid (B) or a powder comprising the tetracalcium phosphate particles (A), the alkali metal salt of phosphoric acid (B), and acidic calcium phosphate particles (C) is mixed beforehand, and it is preferred that at least one device selected from among a jet mill, a pestle and mortar machine, a ball mill, a high-speed rotation mill, a planetary mill, a hybridizer, a mechanofusion machine, or a mixing extruder is used in the mixing.

At this time it is preferred to add a liquid or aqueous paste comprising water as a main ingredient and also comprising the alkali metal salt of phosphoric acid (B) to a powder or nonaqueous paste comprising the tetracalcium phosphate particles (A) and then mix them.

The aforementioned problems are solved by providing a method for producing a dentinal hypersensitivity inhibitor, the method comprising mixing tetracalcium phosphate particles (A), an alkali metal salt of phosphoric acid (B), acidic calcium phosphate particles (C), and a liquid or aqueous paste comprising water as a main ingredient, wherein the dentinal hypersensitivity inhibitor is a material to be used for closing dentinal tubules by rubbing a dentin surface therewith, the tetracalcium phosphate particles (A) has an average particle diameter of 0.5 to 40 µm, 1 to 100 parts by weight of the alkali metal salts of phosphoric acid (B) is blended to 100 parts by weight of the tetracalcium phosphate particles (A), and the blended amount of the tetracalcium phosphate particles (A) relative to 100 parts by weight of the whole amount of the dentinal hypersensitivity inhibitor is adjusted to 5 to 55 parts by weight.

At this time, it is preferred to add a liquid or aqueous paste comprising water as a main ingredient and also comprising the acidic calcium phosphate particles (C) to a powder or nonaqueous paste comprising the tetracalcium phosphate particles (A) and the alkali metal salt of phosphoric acid (B) and then mix them.

The aforementioned problems are solved by providing a method for producing a dentinal hypersensitivity inhibitor, the method comprising mixing tetracalcium phosphate particles (A), an alkali metal salt of phosphoric acid (B), and a liquid or aqueous paste comprising water as a main ingredient, wherein 1 to 100 parts by weight of the alkali metal salts of phosphoric acid (B) is blended to 100 parts by weight of the tetracalcium phosphate particles (A), and the blended amount of the tetracalcium phosphate particles (A) relative to 100 parts by weight of the whole amount of the dentinal hypersensitivity inhibitor is adjusted to 1 to 80 parts by weight, and when a suspension is prepared by adding 0.05 g of the dentinal hypersensitivity inhibitor into 200 g of pure water of 25° C., a free alkali metal ion concentration of the suspension at a time of 10 minutes after the adding is adjusted to 0.2 to 100 mg/L.

Moreover the aforementioned problems are solved by providing a method for inhibiting dentinal hypersensitivity using a dentinal hypersensitivity inhibitor comprising tetracalcium phosphate particles (A), an alkali metal salt of phosphoric acid (B), and acidic calcium phosphate particles (C), wherein a dentin surface is rubbed with the dentinal hypersensitivity inhibitor having the tetracalcium phosphate particles (A) having an average particle diameter of 0.5 to 40 µm, a blended amount of the tetracalcium phosphate particles (A) of 5 to 55 parts by weight relative to 100 parts by weight of the whole amount of the dentinal hypersensitivity inhibitor, and a blended amount of the alkali metal salt of phosphoric acid (B) of 1 to 100 parts by weight relative to 100 parts by weight of the tetracalcium phosphate particles (A).

The aforementioned problems are solved by providing a dentin mineralizing agent kit composed of a powder or non-aqueous paste comprising tetracalcium phosphate particles (A) and an alkali metal salt of phosphoric acid (B) and a liquid or aqueous paste comprising water as a main ingredient.

The aforementioned problems are solved by providing a dentin mineralizing agent kit composed of a powder or non-aqueous paste comprising tetracalcium phosphate particles (A), an alkali metal salt of phosphoric acid (B), and acidic calcium phosphate particles (C) and a liquid or aqueous paste comprising water as a main ingredient.

The aforementioned problems are solved by providing a dentin mineralizing agent kit composed of a powder or non-aqueous paste comprising tetracalcium phosphate particles (A) and a liquid or aqueous paste comprising water as a main ingredient and also comprising an alkali metal salt of phosphoric acid (B).

The aforementioned problems are solved by providing a dentin mineralizing agent kit composed of a powder or non-aqueous paste comprising tetracalcium phosphate particles (A), a powder or nonaqueous paste comprising an alkali metal salt of phosphoric acid (B), and a liquid or aqueous paste comprising water as a main ingredient.

The aforementioned problems are solved by providing a dentinal hypersensitivity inhibitor kit composed of a powder or nonaqueous paste comprising tetracalcium phosphate particles (A) and an alkali metal salt of phosphoric acid (B) and a liquid or aqueous paste comprising water as a main ingredient and also comprising acidic calcium phosphate particles (C).

The aforementioned problems are solved by providing a dentinal hypersensitivity inhibitor kit composed of a powder or nonaqueous paste comprising tetracalcium phosphate particles (A), a powder or nonaqueous paste comprising an alkali metal salt of phosphoric acid (B), a powder or nonaqueous paste comprising acidic calcium phosphate particles (C), and a liquid or aqueous paste comprising water as a main ingredient.

Effect of the Invention

By the present invention is provided a dentin mineralizing agent by which a dense HAp is formed on a dentin surface and HAp is deposited to a deep portion of a dentinal tubule, so that it can close the dentinal tubule. Thanks to this, a false enamel is formed on a dentin surface to impart caries resistance and treatment of hyperesthesia becomes possible.

DETAILED DESCRIPTION OF THE INVENTION

Figure 1:
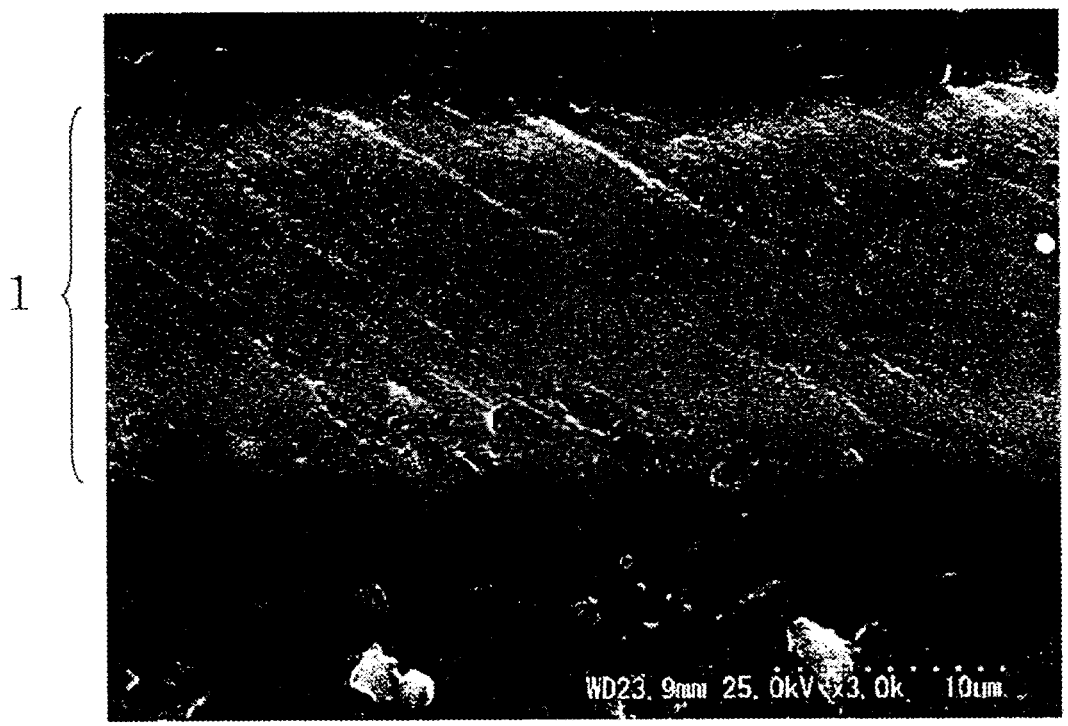
FIG. 1 A SEM photograph of a surface of a bovine dentin in which a HAp layer was formed in Example 1.

The dentin mineralizing agent of the present invention comprises tetracalcium phosphate particles (A) and an alkali metal salt of phosphoric acid (B). If a composition containing tetracalcium phosphate particles (A) is mixed in the presence of water, it will convert into hydroxyapatite slowly. It has been made clear by the present inventors that through the use of a dentin mineralizing agent comprising tetracalcium phosphate particles (A) and an alkali metal salt of phosphoric acid (B) in certain amounts, a mineralization effect is highly achieved and hydroxyapatite deposits to especially deep portions of dentinal tubules, so that the dentinal tubules can be closed. While the reason for this is not necessarily clear, the following mechanism is presumed.

That is, when a dentin mineralizing agent comprising tetracalcium phosphate particles (A) and an alkali metal salt of phosphoric acid (B) in certain amounts is prepared in the presence of water and then is used, it seems that calcium ions produced due to dissolution of the tetracalcium phosphate particles (A) react with phosphorus ions produced due to dissolution of the alkali metal salt of phosphoric acid (B), so that energetically stable HAp is deposited. It seems that as a result a dense HAp layer is formed on a surface of a dentin and HAp is deposited to deep portions of dentinal tubules, so that the dentinal tubules are closed. Thanks to this, a false enamel is formed on a dentin surface to impart caries resistance (prevention of root caries) and treatment of hyperesthesia becomes possible. Moreover, since HAp deposits even to deep portions of dentinal tubules and thereby the dentinal tubules are closed, an apparent dentin mineral concentration increases and wear resistance is also improved. The present inventors have considered that the balance of velocities at which calcium ions and phosphate ions are supplied is important for generating the above-mentioned effect. And they have confirmed that deposition of HAp does not proceed well when the solubility of a compound that supplies calcium ions or a compound that supplies phosphate ions is low or extremely high. Therefore, there is a great significance in adoption of such a constitution of the present invention that supply rates and a supply balance of calcium ions and phosphate ions to dentin become adequate due to inclusion of certain amounts of tetracalcium phosphate particles (A) and an alkali metal salt of phosphoric acid (B).

In the present invention, the tetracalcium phosphate particles (A) in an amount of 1 to 80 parts by weight relative to 100 parts by weight of the whole amount of the dentin mineralizing agent are contained. When the content of the tetracalcium phosphate particles (A) is less than 1 part by weight, a mineralization effect may not be obtained due to inhibition of deposition of HAp; the content is preferably 5 parts by weight or more, more preferably 10 parts by weight or more, and even more preferably 20 parts by weight or more. On the other hand, when the content of the tetracalcium phosphate particles (A) exceeds 80 parts by weight, a mineralization effect may not be obtained due to inhibition of deposition of HAp; the content is preferably 75 parts by weight or less, more preferably 70 parts by weight or less, and even more preferably 60 parts by weight or less.

When the dentin mineralizing agent of the present invention is used as a dentinal hypersensitivity inhibitor, the blended amount of the tetracalcium phosphate particles (A) relative to 100 parts by weight of the whole amount of the dentinal hypersensitivity inhibitor is preferably 5 to 55 parts by weight. When the blended amount of the tetracalcium phosphate particles (A) is less than 5 parts by weight, a capability of closing dentinal tubules may deteriorate due to inhibition of deposition of HAp; the blended amount is preferably 10 parts by weight or more, and more preferably 20 parts by weight or more. On the other hand, when the blended amount of the tetracalcium phosphate particles (A) exceeds 55 parts by weight, a capability of closing dentinal tubules may deteriorate due to inhibition of deposition of HAp; the blended amount is preferably 50 parts by weight or less, and more preferably 45 parts by weight or less.

A method for producing the tetracalcium phosphate $[Ca_4(PO_4)_2O]$ particles (A) to be used in the present invention is not particularly restricted. Commercially available tetracalcium phosphate particles may be used as it is, or alternatively, they may be used after appropriate regulation of their particle size by grinding. As a grinding method, a method which is the same as the grinding method of acidic calcium phosphate particles (C) described below can be used.

It is preferred that an average particle diameter of the tetracalcium phosphate particles (A) to be used in the present invention is from 0.5 to 40 μm. When the average particle diameter is less than 5 μm, the tetracalcium phosphate particles (A) may dissolve excessively, so that the pH of the aqueous solution may become so high that hydroxyapatite does not deposit smoothly and, as a result, a mineralization effect may not be obtained. The average particle diameter of the tetracalcium phosphate particles (A) is more preferably 5 μm or more, and even more preferably 10 μm or more. On the other hand, when the average particle diameter is greater than 40 μm, a paste to be obtained by mixing with a liquid agent may have unsatisfactory paste properties, for example, it may not show a sufficiently high viscosity. Moreover, sandy feeling exhibited in paste mixing may be increased, so that operationality may be impaired, or it may become difficult to remove a paste from a static mixer to be used for mixing. Preferably, the average particle diameter of the tetracalcium phosphate particles (A) is 35 μm or less, and more preferably 30 μm or less. The average particle diameter of the tetracalcium phosphate particles (A) to be used in the present invention is calculated through measurement using a laser diffraction type particle size distribution analyzer.

The dentin mineralizing agent of the present invention contains the alkali metal salt of phosphoric acid (B) in an amount of 1 to 100 parts by weight relative to 100 parts by weight of the tetracalcium phosphate particles (A). Thus, due to the inclusion of a certain amount of the alkali metal salt of phosphoric acid (B) in addition to the tetracalcium phosphate particles (A), it is possible to provide a dentin mineralizing agent that is high in mineralization effect and allows hydroxyapatite to deposit especially to deep portions of dentinal tubules. When the content of the alkali metal salt of phosphoric acid (B) is less than 1 part by weight, a mineralization effect may not be obtained due to inhibition of deposition of HAp; the content is preferably 2 parts by weight or more, and more preferably 5 parts by weight or more. On the other hand, when the content of the alkali metal salt of phosphoric acid (B) exceeds 100 parts by weight, a mineralization effect may not be obtained due to inhibition of deposition of HAp; the content is preferably 98 parts by weight or less, more preferably 95 parts by weight or less, and even more preferably 90 parts by weight or less.

The alkali metal salt of phosphoric acid (B) to be used in the present invention is not particularly restricted, and examples thereof include disodium hydrogen phosphate, dipotassium hydrogen phosphate, lithium dihydrogen phosphate, sodium dihydrogen phosphate, potassium dihydrogen phosphate, trisodium phosphate, tripotassium phosphate, and so on, among which one salt or two or more salts are used. Particularly, from the viewpoint of safety or easiness of obtaining a raw material with high purity, it is preferred that the alkali metal salt of phosphoric acid (B) is disodium hydrogen phosphate and/or sodium dihydrogen phosphate. Moreover, from the viewpoint of safety, it is preferred that the alkali metal ion in the alkali metal salt of phosphoric acid (B) to be used in the present invention is a sodium ion.

It is preferred that an average particle diameter of the alkali metal salt of phosphoric acid (B) to be used in the present invention is from 0.5 to 20 μm. Since when the average particle diameter of the alkali metal salt of phosphoric acid (B) is less than 0.5 μm, it becomes difficult to disperse the salt uniformly in a liquid agent or a powder agent due to the fact that flocculation may become remarkable, when the dentin mineralizing agent of the present invention has converted into hydroxyapatite, a hole may be formed in the hydroxyapatite, so that a dentin penetration inhibition ratio may decrease; therefore the average particle diameter of the alkali metal salt of phosphoric acid (B) is preferably 1 μm or more. On the other hand, in a case where the average particle diameter of the alkali metal salt of phosphoric acid (B) exceeds 20 μm, when the dentin mineralizing agent of the present invention has converted into hydroxyapatite, a hole may be formed in the hydroxyapatite, so that a dentin penetration inhibition ratio may decrease. Particularly, if such a hole is formed in a dentinal tubule, it may become difficult to inhibit hyperesthesia. Moreover, since operationality may deteriorate and also dentin may be damaged due to the increase of sandy feeling resulting from the remaining of undissolved alkali metal salt of phosphoric acid (B) in a paste when inhibiting dentinal hypersensitivity by rubbing the paste to a dentin surface, it is preferred that the average particle diameter of the alkali metal salt of phosphoric acid (B) is 15 μm or less, and it is more preferred to be 10 μm or less.

Preferably, the dentin mineralizing agent of the present invention further contains acidic calcium phosphate particles (C) in addition to the tetracalcium phosphate particles (A) and the alkali metal salt of phosphoric acid (B). This enables it to enhance the mineralization effect. The present inventors presume the reason for this to be that due to the inclusion of the acidic calcium phosphate particles (C) with low solubility in addition to the tetracalcium phosphate particles (A) and the alkali metal salt of phosphoric acid (B), calcium ions and phosphate ions can be supplied for a longer time after the application of the paste and the supply balance becomes more appropriate.

The acidic calcium phosphate particles (C) to be used in the present invention is not particularly restricted, and it is preferred that the acidic calcium phosphate particles (C) are at least one member selected from the group consisting of dicalcium phosphate anhydrous $[CaHPO_4]$ particles, monocalcium phosphate anhydrous $[Ca(H_2PO_4)_2]$ particles, tricalcium phosphate $[Ca_3(PO_4)_2]$ particles, amorphous calcium phosphate $[Ca_3(PO_4)_2 \cdot xH_2O]$ particles, calcium dihydrogen pyrophosphate $[CaH_2P_2O_7]$ particles, dicalcium phosphate dihydrate $[CaHPO_4 \cdot 2H_2O]$ particles, and monocalcium phosphate monohydrate $[Ca(H_2PO_4)_2 \cdot H_2O]$ particles. Among these, at least one member selected from the group consisting of dicalcium phosphate anhydrous $[CaHPO_4]$ particles, monocalcium phosphate anhydrous $[Ca(H_2PO_4)_2]$ particles, dicalcium phosphate dihydrate $[CaHPO_4 \cdot 2H_2O]$ particles, and monocalcium phosphate monohydrate $[Ca(H_2PO_4)_2 \cdot H_2O]$ particles is used more preferably, and particularly, at least one member selected from the group consisting of dicalcium phosphate anhydrous [CaHPO$_4$] particles and monocalcium phosphate anhydrous [Ca(H$_2$PO$_4$)$_2$] particles is used even more preferably.

It is preferable that an average particle diameter of the acidic calcium phosphate particles (C) to be used in the present invention is from 0.1 to 7 μm. When the average particle diameter is less than 0.1 μm, dissolution into a liquid agent proceeds excessively and, as a result, the supply balance between calcium ions and phosphate ions may upset and the viscosity of a paste to be obtained by mixing with a liquid agent may become excessively high; more preferably, the average particle diameter is 0.3 μm or more. On the other hand, when the average particle diameter exceeds 7 μm, the acidic calcium phosphate particles (C) become less soluble in a liquid agent and, therefore, dissolution of the tetracalcium phosphate particles (A) may proceed excessively. As a result, deposition of hydroxyapatite becomes less smooth because the supply balance of calcium ions and phosphate ions comes undone and also because the pH of an aqueous solution becomes high, so that the mineralization effect may deteriorate. The average particle diameter of the acidic calcium phosphate particles (C) is more preferably 3 μm or less. The average particle diameter of the acidic calcium phosphate particles (C) is calculated in the same manner as that for the average particle diameter of the tetracalcium phosphate particles (A).

A method for producing the acidic calcium phosphate particles (C) having such an average particle diameter is not particularly restricted. While commercial products may be used if available, it is often preferable to further grind a commercially available product. In such a case, a grinding machine, such as a ball mill, a pestle and mortar machine and a jet mill, can be used. Acidic calcium phosphate particles (C) can also be obtained by grinding a raw material powder of acidic calcium phosphate together with such a liquid medium as alcohol by the use of a pestle and mortar machine, a ball mill, or the like to prepare a slurry, and drying the obtained slurry. As the grinding machine in this process, a ball mill is preferably used. As the material of its pot and balls, alumina or zirconia is preferably used.

By adjusting the average particle diameter of the tetracalcium phosphate particles (A) to be larger than the average particle diameter of the acidic calcium phosphate particles (C), the balance between the solubilities of both of the materials becomes appropriate and it becomes possible to maintain the pH of an aqueous solution to be almost neutral. As a result, deposition of hydroxyapatite is smoothened, so that the mineralization effect can be enhanced. Specifically, it is more preferable to adjust the average particle diameter of (A) to be not less than twice, even more preferably not less than four times, and particularly preferably not less than seven times the average particle diameter of (C). On the other hand, it is more preferable to adjust the average particle diameter of (A) to be not more than 35 times, even more preferably not more than 30 times, and particularly preferably not more than 25 times the average particle diameter of (C).

While the blending ratio (A/C) of the tetracalcium phosphate particles (A) to the acidic calcium phosphate particles (C) is not particularly restricted, it is preferable for the particles to be used in a blending ratio within the range of from 40/60 to 60/40 in molar ratio. Thanks to this, the dentin mineralizing agent with high mineralization effect of the present invention can be obtained. The blending ratio (A/C) is more preferably from 45/55 to 55/45, and most preferably is substantially 50/50.

Preferably, the dentin mineralizing agent of the present invention further contains a fluorine compound (D). This enables it to impart acid resistance to dentin and also promote mineralization. The fluorine compound (D) to be used in the present invention, is not particularly restricted, and examples thereof include sodium fluoride, potassium fluoride, ammonium fluoride, lithium fluoride, cesium fluoride, magnesium fluoride, calcium fluoride, strontium fluoride, strontium fluoride, barium fluoride, copper fluoride, zirconium fluoride, aluminum fluoride, stannous fluoride, sodium monofluorophosphate, potassium monofluorophosphorate, hydrofluoric acid, titanium sodium fluoride, titanium potassium fluoride, hexylamine hydrofluoride, laurylamine hydrofluoride, glycine hydrofluoride, alanine hydrofluoride, fluorosilanes, and diamine silver fluoride. Among these, sodium fluoride, sodium monofluorophosphate, and stannous fluoride are suitably used from the viewpoint of a mineralization-promoting effect. The used amount of the fluorine compound (D) is not particularly limited, and it is preferred that 0.01 to 3 parts by weight of the fluorine compound (D) in terms of fluoride ion are contained relative to 100 parts by weight of the whole amount of the dentin mineralizing agent. When the used amount of the fluorine compound (D) in terms of fluoride ion is less than 0.01 parts by weight, there is a possibility that the effect of promoting mineralization may deteriorate, and it is more preferred that the used amount is 0.05 parts by weight or more. On the other hand, when the used amount of the converted fluoride ions of the fluorine compound (D) exceeds 3 parts by weight, there is a possibility that safety may be impaired, and it is more preferred that the used amount is 1 part by weight or less.

The dentin mineralizing agent of the present invention may contain components other than the tetracalcium phosphate particle (A), the alkali metal salt of phosphoric acid (B), the acidic calcium phosphate (C), and the fluorine compound (D) as far as the effect of the present invention is not damaged. For example, a thickener may be blended according to need. Specific examples of the thickener may be one or two or more species selected from among carboxymethylcellulose, sodium carboxymethylcellulose, hydroxypropylcellulose, hydroxypropylmethylcellulose, polyvinyl alcohol, polyethylene glycol, polyacrylic acid, polystyrene sulfonic acid, polystyrene sulfonic acid salts, polyglutamic acid, polyglutamic acid salts, polyaspartic acid, polyaspartic acid salts, polyL-lysin, polyL-lysin salts, starch other than cellulose, alginic acid, alginic acid salts, carrageenan, guar gum, xanthan gum, cellulose gum, hyaluronic acid, hyaluronic acid salts, pectin, pectin salts, polysaccharides such as chitin and chitosan, acidic polysaccharide esters such as propylene glycol alginate, and polymers such as proteins, e.g. collagen, gelatin and their derivatives. From aspects of solubility in water and viscosity, at least one species selected from sodium carboxymethylcellulose, hydroxypropylcellulose, hydroxypropylmethylcellulose, alginic acid, alginic acid salts, chitosan, polyglutamic acid and polyglutamic acid salts is preferred. The thickener may be blended with a powder, and may be blended with a liquid agent, and also may be blended with a paste under mixing.

According to need, inorganic fillers typified by silica and metal oxides, polyhydric alcohols, such as glycerol, ethylene glycol, propylene glycol, and diglycerol, sugar alcohols, such as xylitol, sorbitol, and erythritol, polyethers, such as polyethylene glycol and polypropylene glycol, artificial sweeteners, such as aspartame, acesulfame potassium, liquorice extract, saccharin, and saccharin sodium, and so on may also be added. Among these, the dentin mineralizing agent of the present invention preferably contains an inorganic filler, more preferably contains particles (E) of 0.002 to 2 μm in average particle diameter selected from silica or metal oxides, and even more preferably contains silica particles (E) having an average particle diameter of 0.002 to 2 µm.

Moreover, all pharmacologically acceptable drugs can be blended. For example, antibacterial agents typified by cetyl pyridinium chloride etc., disinfectants, anticancer drugs, antibiotics, blood circulation improvers, such as Actosin and PEG1, growth factors, such as bFGF, PDGF, and BMP, cells which promote hard tissue formation, such as osteoblasts, odontoblasts, and anaplastic bone marrow derived stem cells, embryonic stem (ES) cells, induced pluripotent stem (iPS) cells produced by dedifferentiating differentiated cells such as fibroblasts by gene introduction and cells produced by differentiating the foregoing can be blended.

It is preferred for the dentin mineralizing agent of the present invention that when a suspension is prepared by adding 0.05 g of the dentin mineralizing agent into 200 g of pure water of 25° C., a free alkali metal ion concentration of the suspension at a time of 10 minutes after the adding is 0.2 to 100 mg/L. Thanks to that the aforementioned free alkali metal ion concentration is within such a range, there is an advantage that a dentin mineralizing agent good in dentin penetration inhibition ratio can be obtained. When the aforementioned free alkali metal ion concentration is less than 0.2 mg/L, conversion to hydroxyapatite may become less smooth due to shortage of phosphate ions supplied together with alkali metal ions, resulting in a fear that a dentin mineralizing agent good in dentin penetration inhibition ratio is not obtained; it is more preferably 0.5 mg/L or more, even more preferably 1 mg/L or more. On the other hand, when the aforementioned free alkali metal ion concentration exceeds 100 mg/L, conversion to hydroxyapatite may become less smooth due to that phosphate ions are supplied excessively together with alkali metal ions, resulting in a fear that not only a dentin mineralizing agent good in a dentin penetration inhibition ratio is not obtained but also excess sodium ions inhibit conversion to hydroxyapatite; it is more preferably 50 mg/L or less, even more preferably 30 mg/L or less. As the method of measuring free alkali metal ions, any arbitrary method can be chosen. It is possible to collect supernatant of a suspension and then measure it with an ICP emission spectrophotometer or ion chromatography, and it is also permissible to use a measuring method in which an electrode that responds to alkali metal ion concentration is soaked directly in a suspension.

It is preferred for the dentin mineralizing agent of the present invention that a standard deviation σ determined when an average of the free alkali metal ion concentration is expressed by d satisfies σ≤0.3d, in other words, that a value (σ/d) produced by dividing a standard deviation σ by an average d of the free alkali metal ion concentration is 0.3 or less. This improves the uniformity of the alkali metal salt of phosphoric acid (B), and there is an advantage that a dentin mineralizing agent better in dentin penetration inhibition ratio can be obtained. Particularly, since capability of closing dentinal tubules becomes good, there is an advantage that the effect of inhibiting hyperesthesia is enhanced. While the reason for this is not necessarily clear, the following mechanism is presumed. That is, it seems that when the uniformity of the alkali metal salt of phosphoric acid (B) is not good, the alkali metal salt of phosphoric acid (B) is in agglomeration and the agglomerated alkali metal salt of phosphoric acid (B) is incorporated into dentinal tubule together with the dentin mineralizing agent prepared in the presence of water. It is considered that the agglomerated alkali metal salt of phosphoric acid (B) dissolves when the dentin mineralizing agent of the present invention has converted into HAp to form holes in the HAp, so that the dentin penetration inhibition ratio decreases.

It is preferred for the dentin mineralizing agent of the present invention that a dentin penetration inhibition ratio achieved when one side of a 700 µm thick bovine tooth disc is treated with the dentin mineralizing agent satisfies the following formula (1). The dentin mineralizing agent of the present invention that satisfies the following formula (I) has an advantage that false enamel is formed on a dentin surface to impart thereto caries resistance and treatment of hyperesthesia becomes possible because HAp deposits to a deep portion of a dentinal tubule and thereby the dentinal tubule is closed.

$$[1-(\text{penetrated amount of a mineralized bovine tooth disc})/(\text{penetrated amount of an unmineralized bovine tooth disc})] \times 100 \geq 70 \qquad (I).$$

In the present invention, a dentin mineralizing agent in paste form can be obtained by mixing a powder containing tetracalcium phosphate particles (A) and an alkali metal salt of phosphoric acid (B) with a liquid or aqueous paste containing water as a main ingredient. Since this dentin mineralizing agent in paste form containing water starts to develop a reaction of immediate conversion into HAp, it is preferred to be prepared just prior to use at a medical site. A mixing operation is not particularly restricted, and manual mixing and mixing with a static mixer are preferably adopted. The present inventors have confirmed that a mineralization effect is highly achieved if the content of the alkali metal salt of phosphoric acid (B) is within an appropriate range. However, since the solubility of the alkali metal salt of phosphoric acid (B) to water is not so high, the above-mentioned mixing method in which the alkali metal salt of phosphoric acid (B) is added in a powder form is preferably adopted.

A dentin mineralizing agent obtained in such a manner is used preferably, for example, by applying it to a dentin surface. The liquid containing water as a main ingredient may be either pure water or a liquid that contains water as a main ingredient and also contains other ingredients, and the aqueous paste containing water as a main ingredient represents a liquid in paste form that contains water as a main ingredient and also contains other ingredients. The other ingredients are not particularly restricted, and examples thereof include the aforementioned acidic calcium phosphate particles (C), polyhydric alcohols, such as glycerol, ethylene glycol, propylene glycol, and diglycerol, sugar alcohols, such as xylitol, sorbitol, and erythritol, polyethers, such as polyethylene glycol and polypropylene glycol. When acidic calcium phosphate particles (C) are contained as the other ingredient, a method of adding a liquid or aqueous paste comprising water as a main ingredient and also comprising acidic calcium phosphate particles (C) to a powder or nonaqueous paste comprising tetracalcium phosphate particles (A) and an alkali metal salt of phosphoric acid (B) and then mixing them, is also adopted preferably.

Moreover, in the present invention, a dentin mineralizing agent in paste form can be obtained also by add a liquid or aqueous paste comprising water as a main ingredient and also comprising the alkali metal salt of phosphoric acid (B) to a powder or nonaqueous paste comprising the tetracalcium phosphate particles (A) and then mix them. Here, since a reaction in which tetracalcium phosphate particles (A) dissolve to be converted to HAp occurs gradually in the presence of water, it is impossible to store a liquid or aqueous paste comprising water as a main ingredient with tetracalcium phosphate particles (A) having been mixed beforehand. Therefore, a method is preferably adopted in which a powder or a nonaqueous paste comprising a solvent other than water as a main ingredient comprising tetracalcium phosphate particle (A) is mixed with a liquid comprising water as a main ingredient and also comprising an alkali metal salt of phosphoric acid (B), and the method has an advantage that an operation to be done in preparing the agent by mixing just before use is convenient. The solvent other than water to be used for the nonaqueous paste is not particularly restricted, and examples thereof include polyhydric alcohols, such as glycerol, ethylene glycol, propylene glycol, and diglycerol, and polyethers, such as polyethylene glycol and polypropylene glycol.

In the present invention, it is preferred that a powder comprising the tetracalcium phosphate particles (A) and the alkali metal salt of phosphoric acid (B) or a powder comprising the tetracalcium phosphate particles (A), the alkali metal salt of phosphoric acid (B), and acidic calcium phosphate particles (C) is mixed beforehand. Since this makes capability of closing dentinal tubules good, there is an advantage that the effect of inhibiting hyperesthesia is enhanced. Therefore, the dentin mineralizing agent of the present invention is used suitably as a dentinal hypersensitivity inhibitor as described later. Here, it is preferred to use at least one device selected from among a jet mill, a pestle and mortar machine, a ball mill, a high-speed rotation mill, a planetary mill, a hybridizer, a mechanofusion machine, or a mixing extruder, in the mixing. From the viewpoint of enhancing the capability of closing dentinal tubules, it is preferred to use at least one device selected from among a ball mill, a pestle and mortar machine, a high-speed rotation mill, and a jet mill.

The dentin mineralizing agent of the present invention is used suitably for various applications such as a tooth surface-treating material, a dentifrice, or chewing gum. Since a reaction in which tetracalcium phosphate particles (A) dissolve to be converted to HAp occurs gradually in the presence of water, an embodiment in which water is supplied appropriately in use, such as a dentifrice and chewing gum, is permitted and an embodiment in which the agent is mixed appropriately with a liquid agent just prior to use, such as a tooth surface-treating material, is also permitted. Moreover, the dentin mineralizing agent of the present invention can close dentinal tubules through the above-described deposition of HAp to a deep portion of a dentinal tubule; from such a viewpoint, a dentinal hypersensitivity inhibitor composed of the dentin mineralizing agent is a preferred embodiment of the present invention.

It has been revealed by the present inventors that it is possible to close dentinal tubules by at least one treatment by rubbing a dentin surface with a dentinal hypersensitivity inhibitor composed of the dentin mineralizing agent comprising tetracalcium phosphate particles (A) and an alkali metal salt of phosphoric acid (B), wherein the dentinal hypersensitivity inhibitor further comprises acidic calcium phosphate particles (C), the tetracalcium phosphate particles (A) has an average particle diameter of 0.5 to 40 μm, the blended amount of the tetracalcium phosphate particles (A) relative to 100 parts by weight of the whole amount of the dentinal hypersensitivity inhibitor is 5 to 55 parts by weight. While the reason for this is not necessarily clear, the following mechanism is presumed.

That is, when a dentinal hypersensitivity inhibitor containing tetracalcium phosphate particles (A), an alkali metal salt of phosphoric acid (B), and acidic calcium phosphate particles (C) in certain amounts is prepared in the presence of water and then is rubbed into a dentin surface, it seems that calcium ions and phosphate ions supplied from the tetracalcium phosphate particles (A), the alkali metal salt of phosphoric acid (B) and the acidic calcium phosphate particles (C) react together, so that energetically stable HAp is deposited. It seems that at this time the fine crystals of HAp are inserted into dentinal tubules together with a liquid agent containing the dentinal hypersensitivity inhibitor, so that the fine crystals of the HAp inserted into the dentinal tubules are grown due to the calcium ions and the phosphate ions contained in the liquid agent and they become dense to unite with dentin at this time. Since this makes capability of closing dentinal tubules good, the effect of inhibiting hyperesthesia is enhanced.

Therefore, a dentinal hypersensitivity inhibitor characterized by being an agent to be used for closing dentinal tubules by rubbing a dentin surface therewith is a preferred embodiment of the present invention. Moreover, a method for inhibiting dentinal hypersensitivity by rubbing a dentin surface with such a dentinal hypersensitivity inhibitor is also a preferred embodiment of the present invention.

Another preferred embodiment of the present invention is a dentinal hypersensitivity inhibitor composed of the dentin mineralizing agent comprising tetracalcium phosphate particles (A) and an alkali metal salt of phosphoric acid (B), wherein when a suspension is prepared by adding 0.05 g of the dentinal hypersensitivity inhibitor into 200 g of pure water of 25° C., a free alkali metal ion concentration of the suspension at a time of 10 minutes after the adding is 0.2 to 100 mg/L.

The dentin mineralizing agent of the present invention may be in an embodiment that moisture is appropriately supplied in use as mentioned above and also may be in an embodiment that it is mixed appropriately with a liquid agent just before use. Therefore, a dentin mineralizing agent kit composed of a powder or nonaqueous paste comprising tetracalcium phosphate particles (A) and an alkali metal salt of phosphoric acid (B) and a liquid or aqueous paste comprising water as a main ingredient is one of the embodiments of the present invention. Moreover, a dentin mineralizing agent kit composed of a powder or nonaqueous paste comprising tetracalcium phosphate particles (A), an alkali metal salt of phosphoric acid (B), and acidic calcium phosphate particles (C) and a liquid or aqueous paste comprising water as a main ingredient is one of the embodiments of the present invention. Moreover, a dentin mineralizing agent kit composed of a powder or nonaqueous paste comprising tetracalcium phosphate particles (A) and a liquid or aqueous paste comprising water as a main ingredient and also comprising an alkali metal salt of phosphoric acid (B) is one of the embodiments of the present invention. Moreover, a dentin mineralizing agent kit composed of a powder or nonaqueous paste comprising tetracalcium phosphate particles (A), a powder or nonaqueous paste comprising an alkali metal salt of phosphoric acid (B), and a liquid or aqueous paste comprising water as a main ingredient is also one of the embodiments of the present invention.

Furthermore, a dentinal hypersensitivity inhibitor kit composed of a powder or nonaqueous paste comprising tetracalcium phosphate particles (A) and an alkali metal salt of phosphoric acid (B) and a liquid or aqueous paste comprising water as a main ingredient and also comprising acidic calcium phosphate particles (C) is one of the embodiments of the present invention. Moreover, a dentinal hypersensitivity inhibitor kit composed of a powder or nonaqueous paste comprising tetracalcium phosphate particles (A), a powder or nonaqueous paste comprising an alkali metal salt of phosphoric acid (B), a powder or nonaqueous paste comprising acidic calcium phosphate particles (C), and a liquid or aqueous paste comprising water as a main ingredient is also one of the embodiments of the present invention.

EXAMPLES

The present invention is explained below more concretely by way of Examples. In the Examples, as to each of the average particle diameters of tetracalcium phosphate particles (A), alkali metal salt of phosphoric acid (B) particles, acidic calcium phosphate particles (C), and sodium fluoride (D) particles, measurement was conducted using a laser diffraction type particle size distribution analyzer ("SALD-2100" manufactured by Shimadzu Corporation), and a median diameter calculated from the result of the measurement was defined as an average particle diameter.

[Preparation of Bovine Tooth for Mineralization]

A cheek-side center of a healthy bovine incisor tooth was trimmed with #80, #1000 sandpapers by using a rotary grinder, so that dentin was exposed. The ground surface of the bovine tooth disc was further polished with wrapping films (#1200, #3000, #8000, produced by Sumitomo 3M Ltd.) to be smoothened. This dentin portion was masked with manicure with a window of a test portion as large as 7 mm in both the ordinate direction and the abscissa direction (hereinafter referred to as a "dentin window") left unmasked and was air-dried for one hour. As to this bovine tooth, a solution prepared by diluting a 0.5-M EDTA solution (produced by Wako Pure Chemical Industries, Ltd.) five times was applied to the dentin window for 30 seconds to perform demineralization, followed by washing with water for 30 minutes or more. Moreover, it was cleaned by application of a 10% sodium hypochlorite solution (Neo-Cleaner "SEKINE" produced by Neo Dental Chemical Products Co., Ltd.) for two minutes and then was washed in distilled water for about 30 minutes and air-dried for one hour, so that a bovine tooth to be used for mineralization was prepared.

[Preparation of Artificial Saliva]

Sodium chloride (8.77 g, 150 mmol), potassium dihydrogen phosphate (122 mg, 0.9 mmol), calcium chloride (166 mg, 1.5 mmol), and Hepes (4.77 g, 20 mmol) were separately weighed out on weighing dishes and then added one after another to a 2000-ml beaker containing about 800 ml of distilled water. After confirmation of complete dissolution of the solutes, pH was adjusted to 7.0 by dropping a 10% aqueous sodium hydroxide solution while measuring the acidity of the solution with a pH meter (F55, manufactured by HORIBA, Ltd.). Subsequently, this solution was added to a 1000-ml volumetric flask and diluted, so that 1000 ml of artificial saliva was obtained.

Example 1

Preparation of a Dentin Mineralizing Agent (1) Preparation of Tetracalcium Phosphate Particles (A)

The tetracalcium phosphate particles (A1) (average particle diameter=23.1 µm) to be used in this example were prepared by pulverizing crude tetracalcium phosphate prepared by the following procedures. A cake-like equimolar mixture was obtained by adding commercially available dicalcium phosphate anhydrous particles (Product No. 1430, made by J. T. Baker Chemical Co., NJ) and calcium carbonate (Product No. 1288, made by J. T. Baker Chemical Co., NJ) in equimolar amount to water, followed by stirring for one hour, filtering and drying. The cake-like equimolar mixture was heated in an electric furnace (FUS732PB, manufactured by ADVANTEC MFS, INC.) at 1500° C. for 24 hours, and then a tetracalcium phosphate lump was prepared by cooling the mixture to room temperature in a desiccator. The resulting lump was further ground roughly in a mortar and then screened to remove fine powders and tetracalcium phosphate masses, thereby adjusting the particle size to a range of 0.5 to 3 mm, so that crude tetracalcium phosphate was obtained. 100 g of this crude tetracalcium phosphate and 200 g of zirconia ball 20 mm in diameter were added to a 400-ml pulverization pot made of alumina ("Type A-3 HD Pot Mill" manufactured by Nikkato Corporation) and then were pulverized at a rotation speed of 150 rpm for 15 hours, so that tetracalcium phosphate particles (A1) were obtained.

(2) Preparation of Alkali Metal Salt of Phosphoric Acid (B) Particles

As one example of alkali metal salt of phosphoric acid (B) particles, the disodium hydrogen phosphate (B) particles to be used in this Example (1.7 µm in average particle diameter) were obtained in the following manner. A slurry was obtained resulting from addition of 50 g of commercially available disodium hydrogen phosphate particles (produced by Wako Pure Chemical Industries, Ltd.), 240 g of 95% ethanol ("Ethanol (95)" produced by Wako Pure Chemical Industries, Ltd.) and 480 g of zirconia balls having a diameter of 10 mm into a 1000-ml grinding pot made of alumina ("HD-B-104 Pot Mill" manufactured by Nikkato Corporation) and subsequent wet vibration pulverization at a rotation speed of 1500 rpm for 5 hours. Then, the slurry was subjected to evaporation of ethanol with a rotary evaporator, followed by vacuum drying at 60° C. for 6 hours.

(3) Preparation of Acidic Calcium Phosphate Particle (C)

As one example of the acidic calcium phosphate particles (C), the dicalcium phosphate anhydrous particles (C1) to be used in this Example (1.1 µm in average particle diameter) were obtained in the following manner. A slurry was obtained resulting from addition of 50 g of commercially available dicalcium phosphate anhydrous particles (Product No. 1430, produced by J. T. Baker Chemical Co., 10.2 µm in average particle diameter), 240 g of 95% ethanol ("Ethanol (95)" produced by Wako Pure Chemical Industries, Ltd.) and 480 g of zirconia balls having a diameter of 10 mm into a 1000-ml grinding pot made of alumina ("HD-B-104 Pot Mill" manufactured by Nikkato Corp.) and subsequent wet vibration pulverization at a rotation speed of 1500 rpm for 15 hours. Then, the slurry was subjected to evaporation of ethanol with a rotary evaporator, followed by vacuum drying at 60° C. for 6 hours.

(4) Preparation of Powder Agent for Dentin Mineralizing Agent

A powder agent for a dentin mineralizing agent was obtained by adding 26.2 g of the tetracalcium phosphate particles (A1) obtained above, 5 g of disodium hydrogen phosphate (B) particles, 9.8 g of dicalcium phosphate anhydrous particles (C1), and 0.21 g of sodium fluoride (D) particles (average particle diameter=0.7 µm) pulverized by the method disclosed in JP 2-258602 A to a high-speed rotation mill ("SM-1" manufactured by AS ONE Corporation) and then mixing them at a rotation speed of 1000 rpm for 3 minutes. The method for preparing a powder agent in which it is obtained by performing mixing in such a way was named "Method 1."

(5) Preparation of Paste in Liquid Form for Dentin Mineralizing Agent

A paste in liquid form for a dentin mineralizing agent was obtained by emulsifying and dispersing 1000 g of glycerol (produced by Wako Pure Chemical Industries, Ltd.), 500 g of propylene glycol (produced by Wako Pure Chemical Industries, Ltd.), 500 g of xylitol (produced by Wako Pure Chemical Industries, Ltd.), 300 g of polyethylene glycol (Macrogol 400, produced by Sanyo Chemical Industries, Ltd.), 5 g of cetyl pyridinium chloride monohydrate (produced by Wako Pure Chemical Industries, Ltd.), 400 g of silica particles (E) ("AEROSIL 130" produced by Degussa Co., average particle diameter=0.016 µm), and 1174 g of distilled water using a universal mixer (manufactured by Powlex Co., Ltd.).

(6) Preparation of Dentin Mineralizing Agent

A dentin mineralizing agent was prepared by weighing out the powder agent obtained in the above-described (4) in an amount of 0.41 g accurately and then adding thereto 0.59 g of the paste in liquid form obtained in the above-described (5). The composition of the dentin mineralizing agent is summarized in Table 1.

[Measurement of Alkali Metal Ion Concentration]

To 200 g of pure water of 25° C. under stirring on a magnetic stirrer was added 0.05 g of the above-described powder agent for a dentin mineralizing agent. At a time of 10 minutes from the adding of the powder agent, stirring was stopped and the resulting supernatant was collected and filtered through a membrane filter, and then the free sodium ion concentration of the powder agent slurry was measured (n=50) by using an ICP atomic emission spectrometer (IRIS AP, manufactured by Japan Jarrell-Ash). The average (d) of the sodium ion concentration of the powder agent in Example 1 was 10.4 mg/L, and the value ($\sigma$/d) produced by dividing the standard deviation ($\sigma$) of the sodium ion concentration by (d) was 0.06. The results obtained are summarized in Table 1.

[Mineralization Test]

The bovine tooth for mineralization prepared above was immersed in distilled water and left at rest for 30 minutes, and then the dentin mineralizing agent in paste form was applied to a dentin window and then mineralized by performing incubation for 30 minutes under conditions of 37° C., 100% RH. Then, the dentin mineralizing agent was washed away with distilled water, followed by storage in the artificial saliva at 37° C. The application of the dentin mineralizing agent was carried out once a day, continuously seven times in total. The sample was immersed always in the artificial saliva except for the times of the operations of application and removal of the dentin mineralizing agent. The artificial saliva was changed every day (n=5).

[Morphological Evaluation]

(1) Preparation of Epoxy Resin

The preparation of an epoxy resin was performed in accordance with the Luft method, and there was used a method that comprises mixing an epoxy resin and a curing agent uniformly and then adding an accelerator. To a 100-ml disposable cup, 41 ml of Luveak 812 (epoxy resin, produced by Nacalai Tesque, Inc.), 31 ml of Luveak MNA (curing agent, produced by Nacalai Tesque, Inc.), and 10 ml of Luveak DDSA (curing agent, produced by Nacalai Tesque, Inc.) were measured with disposable syringes respectively and added, and then were stirred for 10 minutes. To the resultant was dropped slowly under stirring 1.2 ml of Luveak DMP-30 (accelerator, produced by Nacalai Tesque, Inc.) measured in a disposable syringe, and stirring was continued for additional 10 minutes after the addition, thereby completing the preparation.

(2) Production of Sample for SEM Observation

The mineralized bovine tooth was removed from the artificial saliva and was washed with water, and then it was immersed into a 70% aqueous ethanol solution contained in a vial. Immediately after the immersion, the vial was moved into a desiccator and was placed under a reduced pressure condition for 10 minutes. Then, the vial was taken out from the desiccator and it was attached to a low-speed stirrer (TR-118, manufactured by AS-ONE), followed by stirring at a rotation speed of about 4 rpm for 1 hour. The same operations were performed using a 80% aqueous ethanol solution, a 90% aqueous ethanol solution, a 99% aqueous ethanol solution, and 100% ethanol (twice), wherein the bovine tooth was immersed in the second 100% ethanol continuously for one night. Next day, the same operations were carried out sequentially for a 1:1 mixed solvent of propylene oxide and ethanol and for 100% propylene oxide (twice), wherein the bovine tooth was immersed in the second propylene oxide continuously for one night. Moreover, the same operations were carried out also for a mixed solution of epoxy resin: propylene oxide=1:1, a mixed solution of epoxy resin:propylene oxide=4:1, and 100% epoxy resin (twice). As for these, the immersion time was determined to be two hours. Finally, the bovine tooth sample was put into a plastic container in which an epoxy resin was contained, and a curing reaction was carried out at 45° C. for one day and at 60° C. for two days. After the completion of the curing, the sample was cut together with the polyethylene container along a direction perpendicular to a demineralized surface by using a precision low-speed cutter (ISOMET1000, manufactured by BUEHLER), so that a slice of about 1 mm in thickness having a cross section of a portion to be tested was obtained. This slice was polished with wrapping films (#1200, #3000, #8000, produced by Sumitomo 3M Ltd.) to form a sample for SEM observation (n=5).

(3) SEM Observation

Figure 2:
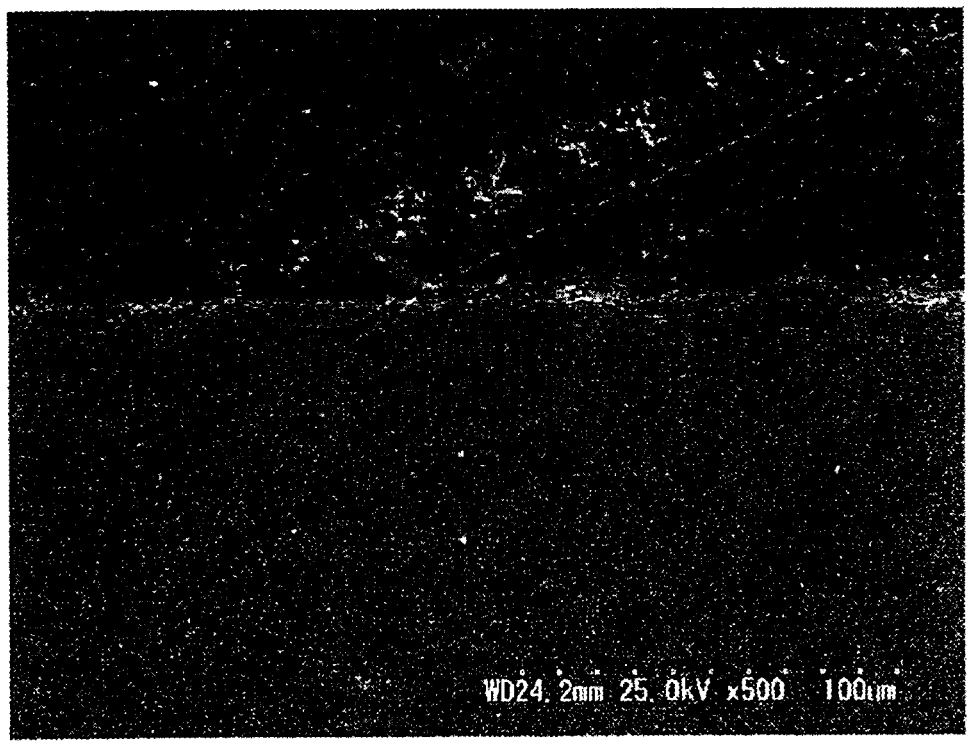
FIG. 2 A SEM photograph in which a surface of a bovine dentin in which dentinal tubules have been closed with HAp is compared with a surface of a bovine dentin in which dentinal tubules are exposed in Example 1.

For SEM measurement was used an S-3500N (manufactured by Hitachi High-Technologies Corporation). The thickness of a hydroxyapatite layer formed on a dentin surface and the deepest distance from a mineralized dentin surface at which distance the closure of dentinal tubules could be observed were measured at an accelerating voltage of 15 kV. The average thickness of the hydroxyapatite layer on the bovine dentin surface mineralized by the above-mentioned dentin mineralizing agent was 16 µm, and the deepest distance at which the dentinal tubule closure by hydroxyapatite could be observed was 323 µm on average. The results obtained are summarized in Table 4. As can be recognized from the SEM photographs of FIG. 1 and FIG. 2, it was confirmed that an HAp layer was formed on a dentin surface and dentinal tubules was closed by HAp as a result of the application of the dentin mineralizing agent of the present invention to the dentin surface.

[Dentin Penetration Inhibition Ratio Evaluation]

(1) Preparation of Bovine Tooth Disc for Mineralization

A cheek-side center of a healthy bovine incisor tooth was trimmed with #80, #1000 sand papers by using a rotary grinder, so that it was shaped into a disc form about 1.5 cm in diameter and 0.9 mm in thickness. The ground surface of the bovine tooth disc was further polished with wrapping films (#1200, #3000, #8000, produced by Sumitomo 3M Ltd.) to have a thickness of 0.7 mm and be smoothened. As to both surfaces of this bovine tooth, a solution prepared by diluting a 0.5-M EDTA solution (produced by Wako Pure Chemical Industries, Ltd.) five times was applied to the dentin window for 180 seconds to perform demineralization, followed by washing with distilled water for about 30 seconds. Moreover, it was cleaned by applying a 10% sodium hypochlorite solution (Neo-Cleaner "SEKINE" produced by Neo Dental Chemical Products Co., Ltd.) to it for 120 seconds and then was washed in distilled water for about 30 minutes, so that a bovine tooth disc to be used for dentin penetration inhibition ratio evaluation was prepared.

(2) Mineralization Test

The bovine tooth disc for mineralization prepared above was immersed in distilled water and left at rest for 30 minutes, and then the dentin mineralizing agent in paste form was applied to one of the disc surfaces (enamel side) and then mineralized by performing incubation for 30 minutes under conditions of 37° C., 100% RH. Then, the dentin mineralizing agent was washed away with distilled water, followed by storage in the artificial saliva at 37° C. The application of the dentin mineralizing agent was carried out to the same surface once a day, continuously seven times in total. The sample was immersed always in the artificial saliva except for the times of the operations of application and removal of the dentin mineralizing agent. The artificial saliva was changed every day (n=5).

(3) Dentin Penetration Inhibition Ratio Evaluation Test

Evaluation of a dentin penetration inhibition ratio was performed using a method according to the method of Pashley et al. (D. H. PASHLEY et al., J. Dent. Res. 65:417-420, 1986; K. C. Y. TAY et al., J. Endod. 33:1438-1443, 2007). The same device was installed, and the mineralized bovine tooth was installed and fixed to a dividable chamber jig so that a liquid could penetrate in a direction from dental pulp toward enamel. The dentin surface to receive pressure of phosphate-buffered saline (Dulbecco's PBS, Grand Island Biological Company, Grand Island, N.Y.) was standardized to a surface area of 78.5 mm$^2$ (5 mm in diameter) using an O ring and was pressurized at 10 psi (69 kPa), and then a penetrated amount was measured after a lapse of 24 hours. Moreover, a penetrated amount of a bovine tooth disc having not been subjected to the mineralization was measured by the same operation, and a penetration inhibition ratio was calculated using the following formula. The penetration inhibition ratio of the bovine tooth disc mineralized by Example 1 was 85%. The results obtained are summarized in Table 4.

Penetration inhibition ratio (%)=(1−(penetrated amount of a mineralized bovine tooth disc)/(penetrated amount of an unmineralized bovine tooth disc)1×100

Example 2

A dentin mineralizing agent was prepared in the same manner as in Example 1 except for failing to use the dicalcium phosphate anhydrous particles (C1) and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 3

A dentin mineralizing agent was prepared in the same manner as in Example 1 except for preparing it by adding the disodium hydrogen phosphate (B) particles to the paste in liquid form instead of by adding to the powder agent in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 4

A dentin mineralizing agent was prepared in the same manner as in Example 1 except for adjusting the used amount of the disodium hydrogen phosphate (B) particles to 0.5 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 5

A dentin mineralizing agent was prepared in the same manner as in Example 1 except for preparing it by adding 0.5 parts by weight of the disodium hydrogen phosphate (B) particles to the paste in liquid form instead of by adding 5 parts by weight of the disodium hydrogen phosphate (B) particles to the powder agent and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, the evaluation results obtained are summarized in Table 4.

Example 6

A dentin mineralizing agent was prepared in the same manner as in Example 1 except for adjusting the used amount of the disodium hydrogen phosphate (B) particles to 25 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 7

A dentin mineralizing agent was prepared in the same manner as in Example 1 except for preparing it by adding 25 parts by weight of the disodium hydrogen phosphate (B) particles to the paste in liquid form instead of by adding 5 parts by weight of the disodium hydrogen phosphate (B) particles to the powder agent and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 8

A dentin mineralizing agent was prepared in the same manner as in Example 1 except for adjusting the used amount of the disodium hydrogen phosphate (B) particles to 2.5 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 9

A dentin mineralizing agent was prepared in the same manner as in Example 1 except for adjusting the used amount of the disodium hydrogen phosphate (B) particles to 12 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 10

A dentin mineralizing agent was prepared in the same manner as in Example 1 except for adjusting the used amount of the disodium hydrogen phosphate (B) particles to 18 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 11

A dentin mineralizing agent was prepared in the same manner as in Example 1 except for adjusting the used amount of the tetracalcium phosphate particles (A1) to 73.5 parts by weight and the used amount of the disodium hydrogen phosphate (B) particles to 14 parts by weight and failing to use the dicalcium phosphate anhydrous particles (C1), glycerol, propylene glycol, xylitol, polyethylene glycol, and the silica particles (E) in and preparing the rest by using purified water Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 12

A dentin mineralizing agent was prepared in the same manner as in Example 1 except for adjusting the used amount of the tetracalcium phosphate particles (A1) to 49 parts by weight and the used amount of the disodium hydrogen phosphate (B) particles to 9.3 parts by weight and failing to use the dicalcium phosphate anhydrous particles (C1), glycerol, propylene glycol, xylitol, polyethylene glycol, and the silica particles (E) and preparing the rest with purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 13

A dentin mineralizing agent was prepared in the same manner as in Example 1 except for adjusting the used amount of the tetracalcium phosphate particles (A1) to 2.62 parts by weight and the used amount of the dicalcium phosphate anhydrous particles (C1) to 0.98 parts by weight, preparing the agent by adding 0.5 parts by weight of disodium hydrogen phosphate (B) particles to the paste in liquid form instead of preparing it by adding 5 parts by weight of the disodium hydrogen phosphate (B) particles to the powder agent, and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 14

A dentin mineralizing agent was prepared in the same manner as in Example 1 except for adjusting the used amount of the tetracalcium phosphate particles (A1) to 2.62 parts by weight, the used amount of the disodium hydrogen phosphate (B) particles to 0.5 parts by weight, and the used amount of the dicalcium phosphate anhydrous particles (C1) to 0.98 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 1, and the evaluation results obtained are summarized in Table 4.

Example 15

A dentin mineralizing agent was prepared in the same manner as in Example 1 except for adjusting the used amount of the tetracalcium phosphate particles (A1) to 5.24 parts by weight, the used amount of the disodium hydrogen phosphate (B) particles to 1 part by weight, and the used amount of the dicalcium phosphate anhydrous particles (C1) to 1.96 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Example 16

A dentin mineralizing agent was prepared in the same manner as in Example 1 except for adjusting the used amount of the tetracalcium phosphate particles (A1) to 13.1 parts by weight, the used amount of the disodium hydrogen phosphate (B) particles to 2.5 parts by weight, and the used amount of the dicalcium phosphate anhydrous particles (C1) to 4.9 parts by weight in and preparing the rest by using purified water Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Example 17

A dentin mineralizing agent was prepared in the same manner as in Example 1 except for using 5 parts by weight of sodium dihydrogen phosphate (B) particles instead of using 5 parts by weight the disodium hydrogen phosphate (B) particles in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Example 18

A dentin mineralizing agent was prepared in the same manner as in Example 1 except for preparing it by adding 5 parts by weight of sodium dihydrogen phosphate (B) particles to the paste in liquid form instead of by adding 5 parts by weight of the disodium hydrogen phosphate (B) particles to the powder agent and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Example 19

A dentin mineralizing agent was prepared in the same manner as in Example 1 except for failing to use the sodium fluoride (D) particles and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Example 20

A dentin mineralizing agent was prepared in the same manner as in Example 1 except for using 12.3 parts by weight of dicalcium phosphate dihydrate particles (C) (average particle diameter=1.2 μm) instead of using 9.8 parts by weight of the dicalcium phosphate anhydrous particles (C1) and preparing the rest with purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4. Here, the above-mentioned dicalcium phosphate dihydrate particles (C) (average particle diameter=1.2 μm) were obtained by the same method as that used for preparing the dicalcium phosphate anhydrous particles (C1) in Example 1 using commercially available dicalcium phosphate dihydrate particles (produced by Wako Pure Chemical Industries, Ltd., average particle diameter=19 μm).

Example 21

A dentin mineralizing agent was prepared in the same manner as in Example 1 except for using 16.7 parts by weight of monocalcium phosphate anhydrous particles (C) (average particle diameter=1.1 μm) instead of using 9.8 parts by weight of the dicalcium phosphate anhydrous particles (C1) and preparing the rest with purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4. Here, the above-mentioned monocalcium phosphate anhydrous particles (C) (average particle diameter=1.1 μm) were obtained by the same method as that used for preparing the dicalcium phosphate anhydrous particles (C1) in Example 1 using commercially available monocalcium phosphate anhydrous particles (produced by Wako Pure Chemical Industries, Ltd., average particle diameter=18 μm).

Example 22

A dentin mineralizing agent was prepared in the same manner as in Example 1 except for using 15.4 parts by weight of calcium dihydrogen pyrophosphate particles (C) (average particle diameter=1.0 μm) instead of using 9.8 parts by weight of the dicalcium phosphate anhydrous particles (C1) and preparing the rest with purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4. Here, the above-mentioned calcium dihydrogen pyrophosphate particles (C) (average particle diameter=1.0 μm) were obtained by the same method as that used for preparing the dicalcium phosphate anhydrous particles (C1) in Example 1 using commercially available calcium dihydrogen pyrophosphate particles (produced by Taihei Chemical Industrial Co., Ltd., average particle diameter=13 μm).

Example 23

A dentin mineralizing agent was prepared in the same manner as in Example 1 except for adjusting the used amount of the tetracalcium phosphate particles (A1) to 18.4 parts by weight and the used amount of the disodium hydrogen phosphate (B) particles to 3.5 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Example 24

A dentin mineralizing agent was prepared by mixing a nonaqueous paste prepared using 26.2 parts by weight of tetracalcium phosphate particles (A1), 0.21 parts by weight of sodium fluoride (D) particles, 0.5 parts by weight of silica particles (E), 18.09 parts by weight of glycerol and 5 parts by weight of propylene glycol with an aqueous paste prepared using 5 parts by weight of disodium hydrogen phosphate (B) particles, 9.8 parts by weight of dicalcium phosphate anhydrous particles (C1), 5 parts by weight of xylitol, 3 parts by weight of polyethylene glycol, 0.05 parts by weight of cetyl pyridinium chloride monohydrate, 3.5 parts by weight of silica particles (E) and prepared the rest by using purified water instead of preparing the powder agent and the paste in liquid form in Example 1, and morphological evaluation and dentin penetration inhibition ratio evaluation were performed. The composition of the dentin mineralizing agent used is summarized in Table 3, and the evaluation results obtained are summarized in Table 4.

Comparative Example 1

A dentin mineralizing agent was prepared in the same manner as in Example 1 except for adjusting the used amount of the disodium hydrogen phosphate (B) particles to 0.2 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Comparative Example 2

A dentin mineralizing agent was prepared in the same manner as in Example 1 except for preparing it by adding 0.2 parts by weight of the disodium hydrogen phosphate (B) particles to the paste in liquid form and preparing the rest by using purified water instead of by adding 5 parts by weight of the disodium hydrogen phosphate (B) particles to the powder agent in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Comparative Example 3

A dentin mineralizing agent was prepared in the same manner as in Example 1 except for adjusting the used amount of the disodium hydrogen phosphate (B) particles to 27 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Comparative Example 4

A dentin mineralizing agent was prepared in the same manner as in Example 1 except for adjusting the used amount of the tetracalcium phosphate particles (A1) to 81.3 parts by weight and the used amount of the disodium hydrogen phosphate (B) particles to 15.5 parts by weight and failing to use the dicalcium phosphate anhydrous particles (C1), glycerol, propylene glycol, xylitol, polyethylene glycol, and the silica particles (E) and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

Comparative Example 5

A dentin mineralizing agent was prepared in the same manner as in Example 1 except for adjusting the used amount of the tetracalcium phosphate particles (A1) to 0.87 parts by weight, the used amount of the disodium hydrogen phosphate (B) particles to 0.17 parts by weight, and the used amount of the dicalcium phosphate anhydrous particles (C1) to 0.33 parts by weight and preparing the rest by using purified water in Example 1, and then measurement of an alkali metal ion concentration, morphological evaluation, and dentin penetration inhibition ratio evaluation were performed. The composition of the dentin mineralizing agent used is summarized in Table 2, and the evaluation results obtained are summarized in Table 4.

TABLE 1

| | | | Example 1 | Example 2 | Example 3 | Example 4 | Example 5 | Example 6 | Example 7 |
|---|---|---|---|---|---|---|---|---|---|
| Powder agent | Tetracalcium phosphate particle (A) | (parts by weight) | 26.2 (A1) | 26.2 (A1) | 26.2 (A1) | 26.2 (A1) | 26.2 (A1) | 26.2 (A1) | 26.2 (A1) |
| | Disodium hydrogen phosphate (B) particle | (parts by weight) | 5 | 5 | — | 0.5 | — | 25 | — |
| | Sodium dihydrogen phosphate (B) particle | (parts by weight) | — | — | — | — | — | — | — |
| | Dicalcium phosphate anhydrous particle (C) | (parts by weight) | 9.8 (C1) | — | 9.8 (C1) | 9.8 (C1) | 9.8 (C1) | 9.8 (C1) | 9.8 (C1) |
| | Dicalcium phosphate dihydrate particle (C) | (parts by weight) | — | — | — | — | — | — | — |
| | Monocalcium phosphate anhydrous particle (C) | (parts by weight) | — | — | — | — | — | — | — |
| | Calcium dihydrogen pyrophosphate particle (C) | (parts by weight) | — | — | — | — | — | — | — |
| | Sodium fluoride (D) particle | (parts by weight) | 0.21 | 0.21 | 0.21 | 0.21 | 0.21 | 0.21 | 0.21 |
| Paste in liquid form | Disodium hydrogen phosphate (B) particle | (parts by weight) | — | — | 5 | — | 0.5 | — | 25 |
| | Sodium dihydrogen phosphate (B) particle | (parts by weight) | — | — | — | — | — | — | — |
| | Glycerol | (parts by weight) | 10 | 10 | 10 | 10 | 10 | 10 | 10 |
| | Propylene glycol | (parts by weight) | 5 | 5 | 5 | 5 | 5 | 5 | 5 |
| | Xylitol | (parts by weight) | 5 | 5 | 5 | 5 | 5 | 5 | 5 |
| | Polyethylene glycol | (parts by weight) | 3 | 3 | 3 | 3 | 3 | 3 | 3 |
| | Cetyl pyridinium chloride | (parts by weight) | 0.05 | 0.05 | 0.05 | 0.05 | 0.05 | 0.05 | 0.05 |
| | Silica particle (E) | (parts by weight) | 4 | 4 | 4 | 4 | 4 | 4 | 4 |
| | Purified water | (parts by weight) | 31.74 | 41.54 | 31.74 | 36.24 | 36.24 | 11.74 | 11.74 |
| Total | | (parts by weight) | 100 | 100 | 100 | 100 | 100 | 100 | 100 |
| Mixing method of powder agent | | | Method 1 | Method 1 | Method 1 | Method 1 | Method 1 | Method 1 | Method 1 |
| Average of alkali metal ion concentration (mg/L) | | | 10.4 | 13.7 | 0.7 | 1.8 | 0.7 | 33.4 | 0.6 |
| Standard deviation of ion concentration ($\sigma$)/Average of ion concentration (d) | | | 0.06 | 0.04 | 0.05 | 0.05 | 0.04 | 0.07 | 0.04 |

TABLE 1-continued

| | | |
|---|---|---|
| Blended amount of (B) to 100 parts by weight of (A) (parts by weight/parts by weight) | 19 19 19 1.9 1.9 95 95 |
| Mixing ratio (A/C) (mol/mol) | 1 — 1 1 1 1 1 |

| | | | Example 8 | Example 9 | Example 10 | Example 11 | Example 12 | Example 13 | Example 14 |
|---|---|---|---|---|---|---|---|---|---|
| Powder agent | Tetracalcium phosphate particle (A) | (parts by weight) | 26.2 (A1) | 26.2 (A1) | 26.2 (A1) | 73.5 (A1) | 49 (A1) | 2.62 (A1) | 2.62 (A1) |
| | Disodium hydrogen phosphate (B) particle | (parts by weight) | 2.5 | 12 | 18 | 14 | 9.3 | — | 0.5 |
| | Sodium dihydrogen phosphate (B) particle | (parts by weight) | — | — | — | — | — | — | — |
| | Dicalcium phosphate anhydrous particle (C) | (parts by weight) | 9.8 (C1) | 9.8 (C1) | 9.8 (C1) | — | — | 0.98 (C1) | 0.98 (C1) |
| | Dicalcium phosphate dihydrate particle (C) | (parts by weight) | — | — | — | — | — | — | — |
| | Monocalcium phosphate anhydrous particle (C) | (parts by weight) | — | — | — | — | — | — | — |
| | Calcium dihydrogen pyrophosphate particle (C) | (parts by weight) | — | — | — | — | — | — | — |
| | Sodium fluoride (D) particle | (parts by weight) | 0.21 | 0.21 | 0.21 | 0.21 | 0.21 | 0.21 | 0.21 |
| Paste in liquid form | Disodium hydrogen phosphate (B) particle | (parts by weight) | — | — | — | — | — | 0.5 | — |
| | Sodium dihydrogen phosphate (B) particle | (parts by weight) | — | — | — | — | — | — | — |
| | Glycerol | (parts by weight) | 10 | 10 | 10 | — | — | 10 | 10 |
| | Propylene glycol | (parts by weight) | 5 | 5 | 5 | — | — | 5 | 5 |
| | Xylitol | (parts by weight) | 5 | 5 | 5 | — | — | 5 | 5 |
| | Polyethylene glycol | (parts by weight) | 3 | 3 | 3 | — | — | 3 | 3 |
| | Cetyl pyridinium chloride | (parts by weight) | 0.05 | 0.05 | 0.05 | 0.05 | 0.05 | 0.05 | 0.05 |
| | Silica particle (E) | (parts by weight) | 4 | 4 | 4 | — | — | 4 | 4 |
| | Purified water | (parts by weight) | 34.24 | 24.74 | 18.74 | 12.24 | 41.44 | 68.64 | 68.64 |
| Total | | (parts by weight) | 100 | 100 | 100 | 100 | 100 | 100 | 100 |
| Mixing method of powder agent | | | Method 1 | Method 1 | Method 1 | Method 1 | Method 1 | Method 1 | Method 1 |
| Average of alkali metal ion concentration (mg/L) | | | 5.9 | 20.6 | 27.3 | 13.2 | 13.3 | 7.4 | 15.8 |
| Standard deviation of ion concentration (σ)/Average of ion concentration (d) | | | 0.04 | 0.04 | 0.05 | 0.05 | 0.05 | 0.06 | 0.06 |
| Blended amount of (B) to 100 parts by weight of (A) (parts by weight/parts by weight) | | | 9.5 | 46 | 69 | 19 | 19 | 19 | 19 |
| Mixing ratio (A/C) (mol/mol) | | | 1 | 1 | 1 | — | — | 1 | 1 |

Tetracalcium phosphate particle (A1): average particle diameter = 23.1 μm

Dicalcium phosphate anhydrous particle (C1): average particle diameter = 1.1 μm

TABLE 2

| | | | Example 15 | Example 16 | Example 17 | Example 18 | Example 19 | Example 20 | Example 21 | Example 22 |
|---|---|---|---|---|---|---|---|---|---|---|
| Powder agent | Tetracalcium phosphate particle (A) | (parts by weight) | 5.24 (A1) | 13.1 (A1) | 26.2 (A1) | 26.2 (A1) | 26.2 (A1) | 26.2 (A1) | 26.2 (A1) | 26.2 (A1) |
| | Disodium hydrogen phosphate (B) particle | (parts by weight) | 1 | 2.5 | — | — | 5 | 5 | 5 | 5 |
| | Sodium dihydrogen phosphate (B) particle | (parts by weight) | — | — | 5 | — | — | — | — | — |
| | Dicalcium phosphate anhydrous particle (C) | (parts by weight) | 1.96 (C1) | 4.9 (C1) | 9.8 (C1) | 9.8 (C1) | 9.8 (C1) | — | — | — |
| | Dicalcium phosphate dihydrate particle (C) | (parts by weight) | — | — | — | — | — | 12.3 | — | — |
| | Monocalcium phosphate anhydrous particle (C) | (parts by weight) | — | — | — | — | — | — | 16.7 | — |
| | Calcium dihydrogen pyrophosphate particle (C) | (parts by weight) | — | — | — | — | — | — | — | 15.4 |
| | Sodium fluoride (D) particle | (parts by weight) | 0.21 | 0.21 | 0.21 | 0.21 | — | 0.21 | 0.21 | 0.21 |

TABLE 2-continued

|  |  |  | | | | | | | | |
|---|---|---|---|---|---|---|---|---|---|---|
| Paste in liquid form | Disodium hydrogen phosphate (B) particle | (parts by weight) | — | — | — | — | — | — | — | — |
| | Sodium dihydrogen phosphate (B) particle | (parts by weight) | — | — | — | 5 | — | — | — | — |
| | Glycerol | (parts by weight) | 10 | 10 | 10 | 10 | 10 | 10 | 10 | 10 |
| | Propylene glycol | (parts by weight) | 5 | 5 | 5 | 5 | 5 | 5 | 5 | 5 |
| | Xylitol | (parts by weight) | 5 | 5 | 5 | 5 | 5 | 5 | 5 | 5 |
| | Polyethylene glycol | (parts by weight) | 3 | 3 | 3 | 3 | 3 | 3 | 3 | 3 |
| | Cetyl pyridinium chloride | (parts by weight) | 0.05 | 0.05 | 0.05 | 0.05 | 0.05 | 0.05 | 0.05 | 0.05 |
| | Silica particle (E) | (parts by weight) | 4 | 4 | 4 | 4 | 4 | 4 | 4 | 4 |
| | Purified water | (parts by weight) | 64.54 | 52.24 | 31.74 | 31.74 | 31.95 | 29.24 | 24.84 | 26.14 |
| Total | | (parts by weight) | 100 | 100 | 100 | 100 | 100 | 100 | 100 | 100 |
| Mixing method of powder agent | | | Method 1 | Method 1 | Method 1 | Method 1 | Method 1 | Method 1 | Method 1 | Method 1 |
| Average of alkali metal ion concentration (mg/L) | | | 12.9 | 11 | 6.4 | 0.8 | 9.7 | 9.8 | 8.9 | 9.1 |
| Standard deviation of ion concentration ($\sigma$)/Average of ion concentration (d) | | | 0.05 | 0.05 | 0.06 | 0.04 | 0.05 | 0.06 | 0.05 | 0.05 |
| Blended amount of (B) to 100 parts by weight of (A) (parts by weight/parts by weight) | | | 19 | 19 | 19 | 19 | 19 | 19 | 19 | 19 |
| Mixing ratio (A/C) (mol/mol) | | | 1 | 1 | 1 | 1 | 1 | 1 | 1 | 1 |

|  |  |  | Example 23 | Comparative Example 1 | Comparative Example 2 | Comparative Example 3 | Comparative Example 4 | Comparative Example 5 |
|---|---|---|---|---|---|---|---|---|
| Powder agent | Tetracalcium phosphate particle (A) | (parts by weight) | 18.4 (A1) | 26.2 (A1) | 26.2 (A1) | 26.2 (A1) | 81.3 (A1) | 0.87 (A1) |
| | Disodium hydrogen phosphate (B) particle | (parts by weight) | 3.5 | 0.2 | — | 27 | 15.5 | 0.17 |
| | Sodium dihydrogen phosphate (B) particle | (parts by weight) | — | — | — | — | — | — |
| | Dicalcium phosphate anhydrous particle (C) | (parts by weight) | 9.8 (C1) | 9.8 (C1) | 9.8 (C1) | 9.8 (C1) | — | 0.33 (C1) |
| | Dicalcium phosphate dihydrate particle (C) | (parts by weight) | — | — | — | — | — | — |
| | Monocalcium phosphate anhydrous particle (C) | (parts by weight) | — | — | — | — | — | — |
| | Calcium dihydrogen pyrophosphate particle (C) | (parts by weight) | — | — | — | — | — | — |
| | Sodium fluoride (D) particle | (parts by weight) | 0.21 | 0.21 | 0.21 | 0.21 | 0.21 | 0.21 |
| Paste in liquid form | Disodium hydrogen phosphate (B) particle | (parts by weight) | — | — | 0.2 | — | — | — |
| | Sodium dihydrogen phosphate (B) particle | (parts by weight) | — | — | — | — | — | — |
| | Glycerol | (parts by weight) | 10 | 10 | 10 | 10 | — | 10 |
| | Propylene glycol | (parts by weight) | 5 | 5 | 5 | 5 | — | 5 |
| | Xylitol | (parts by weight) | 5 | 5 | 5 | 5 | — | 5 |
| | Polyethylene glycol | (parts by weight) | 3 | 3 | 3 | 3 | — | 3 |
| | Cetyl pyridinium chloride | (parts by weight) | 0.05 | 0.05 | 0.05 | 0.05 | 0.05 | 0.05 |
| | Silica particle (E) | (parts by weight) | 4 | 4 | 4 | 4 | — | 4 |
| | Purified water | (parts by weight) | 41.04 | 36.54 | 36.54 | 9.74 | 2.94 | 71.37 |
| Total | | (parts by weight) | 100 | 100 | 100 | 100 | 100 | 100 |
| Mixing method of powder agent | | | Method 1 | Method 1 | Method 1 | Method 1 | Method 1 | Method 1 |
| Average of alkali metal ion concentration (mg/L) | | | 9.7 | 1.1 | 0.7 | 34.9 | 13.1 | 26.8 |
| Standard deviation of ion concentration ($\sigma$)/Average of ion concentration (d) | | | 0.05 | 0.05 | 0.04 | 0.08 | 0.06 | 0.05 |

TABLE 2-continued

|  | | | | | | |
|---|---|---|---|---|---|---|
| Blended amount of (B) to 100 parts by weight of (A) (parts by weight/parts by weight) | 19 | 0.8 | 0.8 | 103 | 19 | 19 |
| Mixing ratio (A/C) (mol/mol) | 0.7 | 1 | 1 | 1 | — | 1 |

Tetracalcium phosphate particle (A1): average particle diameter = 23.1 μm
Dicalcium phosphate anhydrous particle (C1): average particle diameter = 1.1 μm
Dicalcium phosphate dihydrate particle (C): average particle diameter = 1.2 μm
Monocalcium phosphate anhydrous particle (C): average particle diameter = 1.1 μm
Calcium dihydrogen pyrophosphate particle (C): average particle diameter = 1.0 μm

TABLE 3

|  |  |  | Example 24 | Example 49 |
|---|---|---|---|---|
| Nonaqueous paste | Tetracalcium phosphate particle (A) | (parts by weight) | 26.2 (A1) | 36.5 A4 |
|  | Sodium fluoride (D) particle | (parts by weight) | 0.21 | 0.21 |
|  | Silica particle (E) | (parts by weight) | 0.5 | 2 |
|  | Glycerol | (parts by weight) | 18.09 | 6.29 |
|  | Propylene glycol | (parts by weight) | 5 | 5 |
| Aqueous paste | Disodium hydrogen phosphate (B) particle | (parts by weight) | 5 | 5 |
|  | Sodium dihydrogen phosphate (B) particle | (parts by weight) | — | — |
|  | Dicalcium phosphate anhydrous particle (C) | (parts by weight) | 9.8 (C1) | 13.5 (C1) |
|  | Xylitol | (parts by weight) | 5 | 5 |
|  | Polyethylene glycol | (parts by weight) | 3 | 3 |
|  | Cetyl pyridinium chloride | (parts by weight) | 0.05 | 0.05 |
|  | Silica particle (E) | (parts by weight) | 3.5 | 2 |
|  | Purified water | (parts by weight) | 23.65 | 21.45 |
|  | Total | (parts by weight) | 100 | 100 |
| Blended amount of (B) to 100 parts by weight of (A) (parts by weight/parts by weight) | | | 19 | 19 |
| Mixing ratio (A/C) (mol/mol) | | | 1 | 1 |

Tetracalcium phosphate particle (A1): average particle diameter = 23.1 μm
Dicalcium phosphate anhydrous particle (C1): average particle diameter = 1.1 μm

TABLE 4

|  | Morphological evaluation | | Penetration |
|---|---|---|---|
|  | HAp layer thickness (μm) | HAp mineralization depth (μm) | inhibition ratio (%) |
| Example 1 | 16 | 323 | 85 |
| Example 2 | 3 | 126 | 29 |
| Example 3 | 13 | 268 | 77 |
| Example 4 | 7 | 191 | 43 |
| Example 5 | 6 | 185 | 41 |
| Example 6 | 11 | 350 | 80 |
| Example 7 | 13 | 335 | 78 |
| Example 8 | 10 | 252 | 64 |
| Example 9 | 15 | 331 | 83 |
| Example 10 | 13 | 342 | 81 |
| Example 11 | 12 | 212 | 51 |
| Example 12 | 13 | 254 | 63 |
| Example 13 | 8 | 185 | 42 |
| Example 14 | 7 | 180 | 39 |
| Example 15 | 9 | 219 | 46 |
| Example 16 | 11 | 258 | 61 |
| Example 17 | 9 | 221 | 53 |
| Example 18 | 11 | 259 | 74 |
| Example 19 | 13 | 305 | 79 |
| Example 20 | 15 | 320 | 84 |
| Example 21 | 9 | 361 | 81 |
| Example 22 | 10 | 349 | 82 |
| Example 23 | 15 | 302 | 79 |
| Example 24 | 16 | 330 | 83 |
| Comparative Example 1 | Not observed | 25 | 3 |
| Comparative Example 2 | Not observed | 19 | 2 |
| Comparative Example 3 | 3 | 75 | 17 |
| Comparative Example 4 | 8 | 60 | 15 |
| Comparative Example 5 | Not observed | 16 | 4 |

Example 25

Preparation of Dentinal Hypersensitivity Inhibitor (1) Preparation of Tetracalcium Phosphate Particles (A)

The tetracalcium phosphate particles (A4) (average particle diameter=5.2 μm) to be used in this example were prepared by pulverizing crude tetracalcium phosphate prepared by the following procedures. A cake-like equimolar mixture was obtained by adding commercially available dicalcium phosphate anhydrous particles (Product No. 1430, made by J. T. Baker Chemical Co., NJ) and calcium carbonate (Product No. 1288, made by J. T. Baker Chemical Co., NJ) in equimolar amount to water, followed by stirring for one hour, filtering and drying. The cake-like equimolar mixture was heated in an electric furnace (FUS732PB, manufactured by ADVANTEC MFS, INC.) at 1500° C. for 24 hours, and then a tetracalcium phosphate lump was prepared by cooling the mixture to room temperature in a desiccator. The resulting lump was further ground roughly in a mortar and then screened to remove fine powders and tetracalcium phosphate masses, thereby adjusting the particle size to a range of 0.5 to 1 mm, so that crude tetracalcium phosphate was obtained. A slurry was obtained by adding 50 g of the crude tetracalcium phosphate, 200 g of zirconia ball 10 mm in diameter, and 100 g of 99.5% dehydrated ethanol ("Ethanol, Dehydrated (99.5)" produced by Wako Pure Chemical Industries, Ltd.) to a 1000-ml pulverization pot made of alumina ("HD-B-104 Pot Mill" manufactured by Nikkato Corporation) and then subjecting them to wet vibration pulverization at a rotation speed of 1500 rpm for 12 hours. The slurry was subjected to removal of ethanol by using a rotary evaporator and then vacuum dried at 60° C. for 6 hours, so that tetracalcium phosphate particles (A4) were obtained.

Moreover, tetracalcium phosphate particles (A2) having an average particle diameter of 35.6 μm were obtained by changing the pulverization time in the preparation of the tetracalcium phosphate particles (A4) to 1 hour. Similarly, tetracalcium phosphate particles (A3) having an average particle diameter of 20.3 μm were obtained by changing the pulverization time in the preparation of the tetracalcium phosphate particles (A4) to 4 hours. Similarly, tetracalcium phosphate particles (A5) having an average particle diameter of 1.5 μm were obtained by changing the pulverization time in the preparation of the tetracalcium phosphate particles (A4) to 24 hours.

(2) Preparation of Alkali Metal Salt of Phosphoric Acid (B) Particles

The disodium hydrogen phosphate (B) particles to be used in this Example (1.7 μm in average particle diameter) were obtained in the following manner. A slurry was obtained resulting from addition of 50 g of commercially available disodium hydrogen phosphate particles (produced by Wako Pure Chemical Industries, Ltd.), 240 g of 95% ethanol ("Ethanol (95)" produced by Wako Pure Chemical Industries, Ltd.) and 480 g of zirconia balls having a diameter of 10 mm into a 1000-ml grinding pot made of alumina ("HD-B-104 Pot Mill" manufactured by Nikkato Corporation) and subsequent wet vibration pulverization at a rotation speed of 1500 rpm for 5 hours. Then, the slurry was subjected to evaporation of ethanol with a rotary evaporator, followed by vacuum drying at 60° C. for 6 hours.

(3) Preparation of Acidic Calcium Phosphate Particle (C)

The dicalcium phosphate anhydrous particles (C1) to be used in this Example (1.1 μm in average particle diameter) were obtained in the following manner. A slurry was obtained resulting from addition of 50 g of commercially available dicalcium phosphate anhydrous particles (Product No. 1430, produced by J. T. Baker Chemical Co., 10.2 μm in average particle diameter), 240 g of 95% ethanol ("Ethanol (95)" produced by Wako Pure Chemical Industries, Ltd.) and 480 g of zirconia balls having a diameter of 10 mm into a 1000-ml grinding pot made of alumina ("HD-B-104 Pot Mill" manufactured by Nikkato Corp.) and subsequent wet vibration pulverization at a rotation speed of 1500 rpm for 15 hours. Then, the slurry was subjected to evaporation of ethanol with a rotary evaporator, followed by vacuum drying at 60° C. for 6 hours.

(4) Preparation of Powder Agent for Dentinal Hypersensitivity Inhibitor

A powder agent for a dentinal hypersensitivity inhibitor was obtained by adding 36.5 g of the tetracalcium phosphate particles (A4) obtained above, 5 g of disodium hydrogen phosphate (B) particles, 13.5 g of dicalcium phosphate anhydrous particles (C1), and 0.21 g of sodium fluoride (D) particles (average particle diameter=0.7 μm) pulverized by the method disclosed in JP 2-258602 A to a high-speed rotation mill ("SM-1" manufactured by AS ONE Corporation) and then mixing them at a rotation speed of 1000 rpm for 3 minutes. The method for preparing a powder agent in which it is obtained by performing mixing in such a way was named "Method 1."

(5) Preparation of Paste in Liquid Form for Dentinal Hypersensitivity Inhibitor

A paste in liquid form for a dentinal hypersensitivity inhibitor was obtained by stirring and mixing 0.5 g of cetyl pyridinium chloride monohydrate (produced by Wako Pure Chemical Industries, Ltd.), 20 g of silica particles (E) ("AEROSIL 130" produced by Degussa Co., 0.016 μm in average particle diameter) and 427.4 g of distilled water for 5 hours.

(6) Preparation of Dentinal Hypersensitivity Inhibitor

A dentinal hypersensitivity inhibitor was prepared by weighing out the powder agent obtained in the above-described (4) in an amount of 0.55 g accurately and then adding thereto 0.45 g of the paste in liquid form obtained in the above-described (5). The composition of the dentinal hypersensitivity inhibitor is summarized in Table 5.

[Measurement of Alkali Metal Ion Concentration]

To 200 g of pure water of 25° C. under stirring on a magnetic stirrer was added 0.05 g of the powder agent for a dentinal hypersensitivity inhibitor obtained by the above-described Method 1. At a time of 10 minutes from the adding of the powder agent, stirring was stopped and the resulting supernatant was collected and filtered through a membrane filter, and then the free sodium ion concentration of the powder agent slurry was measured (n=50) by using an ICP atomic emission spectrometer (IRIS AP, manufactured by Japan Jarrell-Ash). The average (d) of the sodium ion concentration of the powder agent in Example 25 was 7.7 mg/L, and the value (σ/d) produced by dividing the standard deviation (σ) of the sodium ion concentration by (d) was 0.04. The results obtained are summarized in Table 5.

[Dentin Penetration Inhibition Ratio Evaluation]

(1) Production of Bovine Tooth for Dentin Penetration Inhibition Ratio Evaluation A cheek-side dentin of a healthy bovine incisor tooth was trimmed with #80, #1000 sand papers by using a rotary grinder, so that a bovine tooth disc about 1.5 cm in diameter and 0.9 mm in thickness was produced. The surface of the bovine tooth disc was further polished with wrapping films (#1200, #3000, #8000, produced by Sumitomo 3M Ltd.) to have a thickness of 0.7 mm and be smoothened. The resulting bovine tooth disc was immersed in a solution prepared by diluting a 0.5 M EDTA solution (produced by Wako Pure Chemical Industries, Ltd.) five times, for 180 seconds and was washed in distilled water for about 30 seconds. It was further immersed in a 10% sodium hypochlorite solution (Neo-Cleaner "SEKINE" produced by Neo Dental Chemical Products Co., Ltd.) for 120 seconds and then was washed in distilled water for about 30 minutes, so that a bovine tooth disc to be used for dentin penetration inhibition ratio evaluation was prepared.

About 0.1 g of the dentinal hypersensitivity inhibitor prepared above was attached with a spatula to the cheek-side dentin surface of the above-described bovine tooth disc, and then it was rubbed to a dentin of 5 mm in diameter within the center portion of the treated dentin surface, for 30 seconds by using a microbrush ("REGULAR SIZE (2.0 mm), MRB400" produced by MICROBRUSH INTERNATIONAL). Then, the paste on the dentin surface was removed with distilled water, and a dentin penetration inhibition ratio evaluation test (n=5) was carried out immediately.

(2) Dentin Penetration Inhibition Ratio Evaluation Test

Measurement of a dentin penetration inhibition ratio was performed using a method according to the method of Pashley et al. (D. H. PASHLEY et al., J. Dent. Res. 65:417-420, 1986; K. C. Y. TAY et al., J. Endod. 33:1438-1443, 2007). The same device was installed, and the bovine tooth disc having been subjected to the hyperesthesia inhibition treatment was installed and fixed to a dividable chamber jig so that a liquid could penetrate in a direction from dental pulp toward enamel. The dentin surface to receive pressure of phosphate-buffered saline (Dulbecco's PBS, Grand Island Biological Company, Grand Island, N.Y.) was standardized to a surface area of 78.5 mm$^2$ (5 mm in diameter) using an O ring and was pressurized at 10 psi (69 kPa), and then a penetrated amount was measured after a lapse of 24 hours. Moreover, a penetrated amount of a bovine tooth disc having not been subjected to the mineralization (dentinal tubule closure) treatment was measured by the same operation, and a penetration inhibition ratio was calculated using the following formula. The penetration inhibition ratio of the bovine tooth disc mineralized (dentinal tubule-closed) by Example 25 was 92%. The results obtained are summarized in Table 7.

> Penetration inhibition ratio (%)={1−(penetrated amount of a mineralized (dentinal tubule-closed) bovine tooth disc)/(penetrated amount of an unmineralized (dentinal tubule-unclosed) bovine tooth disc)}×100

[Morphological Evaluation]
(1) Production of Bovine Tooth for Morphological Evaluation A cheek-side center of a healthy bovine incisor tooth was trimmed with #80, #1000 sand papers by using a rotary grinder, so that a 2 mm thick dentin plate with a cheek-side dentin exposed was produced. This cheek-side dentin surface was further polished with wrapping films (#1200, #3000, #8000, produced by Sumitomo 3M Ltd.) to be smoothened. This cheek-side dentin portion was masked with manicure with a window of a test portion as large as 7 mm in both the ordinate direction and the abscissa direction left unmasked, and then was air-dried for one hour. As to this bovine tooth, a solution prepared by diluting a 0.5-M EDTA solution (produced by Wako Pure Chemical Industries, Ltd.) five times was applied to the dentin window for 30 seconds to perform demineralization, followed by washing with water for 30 minutes or more. Moreover, it was cleaned by applying a 10% sodium hypochlorite solution (Neo-Cleaner "SEKINE" produced by Neo Dental Chemical Products Co., Ltd.) to it for two minutes and then was washed in water for about 30 minutes or more, so that a bovine tooth to be used for mineralization (dentinal tubule closure) evaluation was prepared. After the above-described tooth surface treatment, half of the tooth surface along the ordinate direction of the tooth was masked with manicure, so that its untreated state was maintained. About 0.1 g of the dentinal hypersensitivity inhibitor prepared above was attached with a spatula to the cheek-side dentin surface of the above-described bovine tooth, and then it was rubbed to the entire dentin window for 30 seconds by using a microbrush ("REGULAR SIZE (2.0 mm), MRB400" produced by MICROBRUSH INTERNATIONAL). Then, the paste on the dentin surface was removed with distilled water (n=10).

(2) Production of Sample for SEM Observation

After the above-described treatment, the bovine tooth sample was immersed in a 70% aqueous ethanol solution in a vial. Immediately after the immersion, the vial was moved into a desiccator and was placed under a reduced pressure condition for 10 minutes. Then, the vial was taken out from the desiccator and it was attached to a low-speed stirrer (TR-118, manufactured by AS-ONE), followed by stirring at a rotation speed of about 4 rpm for 1 hour. The same operations were performed using a 80% aqueous ethanol solution, a 90% aqueous ethanol solution, a 99% aqueous ethanol solution, and 100% ethanol (twice), wherein the bovine tooth was immersed in the second 100% ethanol continuously for one night. Next day, the same operations were carried out sequentially for a 1:1 mixed solvent of propylene oxide and ethanol and for 100% propylene oxide (twice), wherein the bovine tooth was immersed in the second propylene oxide continuously for one night, so that dehydration and removal of the manicure were performed. The sample from which propylene oxide had been evaporated away was determined as a sample for morphological observation of a mineralization (dentinal tubule closure)-treated surface of the bovine tooth disc. Moreover, after the evaporation of propylene oxide, the mineralization (dentinal tubule closure)-treated dentin was fractured brittly by using two pliers, thereby obtaining a sample for morphological observation of a cross section of the dentin.

(3) SEM Observation

Figure 3:
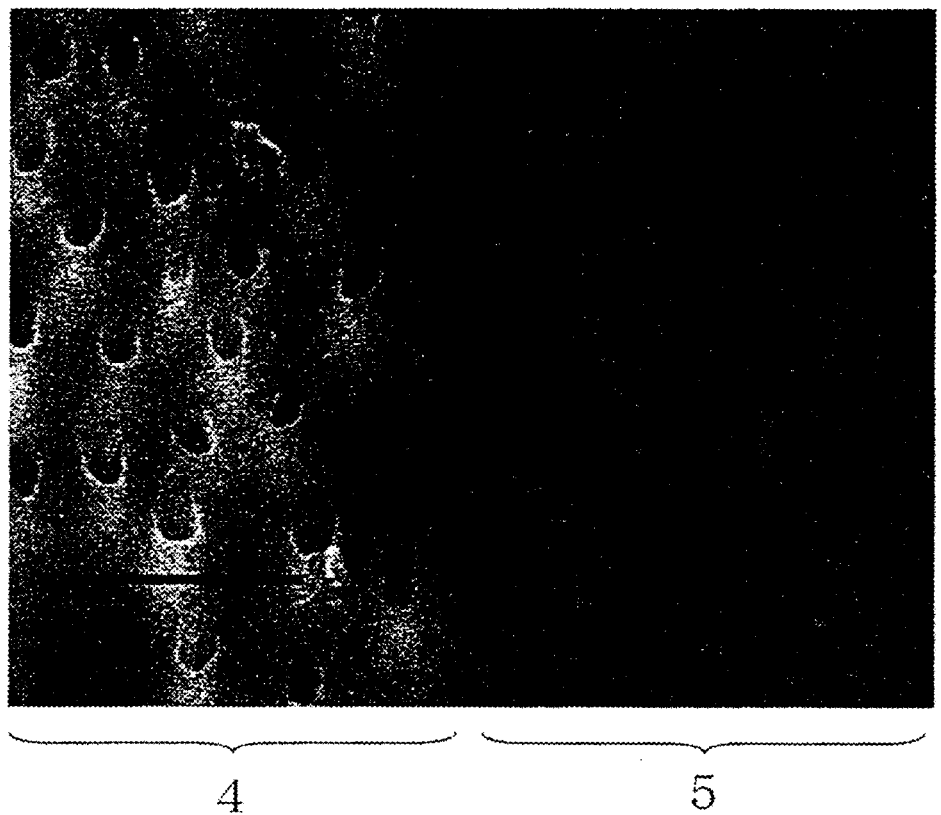
FIG. 3 A SEM photograph in which a surface of a bovine dentin in which dentinal tubules have been closed with HAp is compared with a surface of a bovine dentin in which dentinal tubules are exposed in Example 25.
Figure 4:
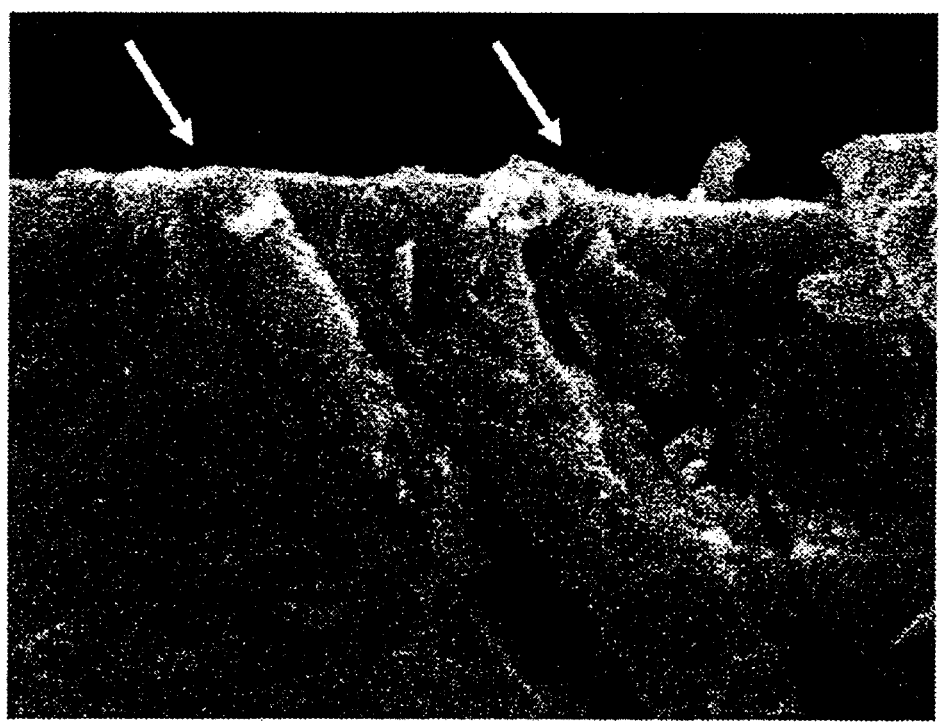
[FIG. 4] A SEM photograph of a cross section of a bovine dentin in which dentinal tubules were closed with HAp in Example 25.

For SEM observation was used an S-3500N (manufactured by Hitachi High-Technologies Corporation). The surface morphology in the vicinity of a boundary between a mineralization (dentinal tubule closure)-treated portion and an untreated portion of a bovine tooth disc before fracture and the morphology in the vicinity of a mineralization (dentinal tubule closure)-treated surface of a cross section of the dentin were observed at an accelerating voltage of 15 kV, and a deepest distance from a mineralized dentin surface at which distance closure by a hypersensitivity inhibitor could be observed in the dentinal tubule direction (hereinafter sometimes referred to also as a "dentinal tubule closure depth") was measured. The average of the dentinal tubule closure depth by the hypersensitivity inhibitor of Example 25 was 15 μm. The results obtained are summarized in Table 7, and the SEM photographs obtained are summarized in FIG. 3 and FIG. 4 (the arrow drawn in FIG. 4 indicates dentinal tubules closed by HAp).

Example 26

A dentinal hypersensitivity inhibitor was prepared in the same manner as in Example 25 except for preparing it by adding the disodium hydrogen phosphate (B) particles to the paste in liquid form instead of by adding to the powder agent in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 27

A dentinal hypersensitivity inhibitor was prepared in the same manner as in Example 25 except for adjusting the used amount of the disodium hydrogen phosphate (B) particles to 0.15 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 28

A dentinal hypersensitivity inhibitor was prepared in the same manner as in Example 25 except for adjusting the used amount of the disodium hydrogen phosphate (B) particles to 0.3 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 29

A dentinal hypersensitivity inhibitor was prepared in the same manner as in Example 25 except for adjusting the used amount of the disodium hydrogen phosphate (B) particles to 2.5 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 30

A dentinal hypersensitivity inhibitor was prepared in the same manner as in Example 25 except for adjusting the used amount of the disodium hydrogen phosphate (B) particles to 20 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 31

A dentinal hypersensitivity inhibitor was prepared in the same manner as in Example 25 except for adjusting the used amount of the tetracalcium phosphate particles (A4) to 21.9 parts by weight, the used amount of the disodium hydrogen phosphate (B) particles to 21 parts by weight, and the used amount of the dicalcium phosphate anhydrous particles (C1) to 8.1 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 32

A dentinal hypersensitivity inhibitor was prepared in the same manner as in Example 25 except for adjusting the used amount of the tetracalcium phosphate particles (A4) to 21.9 parts by weight, the used amount of the disodium hydrogen phosphate (B) particles to 27 parts by weight, and the used amount of the dicalcium phosphate anhydrous particles (C1) to 8.1 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 33

A dentinal hypersensitivity inhibitor was prepared in the same manner as in Example 25 except for adjusting the used amount of the tetracalcium phosphate particles (A4) to 5.5 parts by weight, the used amount of the disodium hydrogen phosphate (B) particles to 0.75 parts by weight, and the used amount of the dicalcium phosphate anhydrous particles (C1) to 2 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 34

A dentinal hypersensitivity inhibitor was prepared in the same manner as in Example 25 except for adjusting the used amount of the tetracalcium phosphate particles (A4) to 7.5 parts by weight, the used amount of the disodium hydrogen phosphate (B) particles to 1.03 parts by weight, and the used amount of the dicalcium phosphate anhydrous particles (C1) to 2.8 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 35

A dentinal hypersensitivity inhibitor was prepared in the same manner as in Example 25 except for adjusting the used amount of the tetracalcium phosphate particles (A4) to 15 parts by weight, the used amount of the disodium hydrogen phosphate (B) particles to 2.06 parts by weight, and the used amount of the dicalcium phosphate anhydrous particles (C1) to 5.6 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 36

A dentinal hypersensitivity inhibitor was prepared in the same manner as in Example 25 except for adjusting the used amount of the tetracalcium phosphate particles (A4) to 50 parts by weight, the used amount of the disodium hydrogen phosphate (B) particles to 6.86 parts by weight, and the used amount of the dicalcium phosphate anhydrous particles (C1) to 18.6 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 37

A dentinal hypersensitivity inhibitor was prepared in the same manner as in Example 25 except for adjusting the used amount of the disodium hydrogen phosphate (B) particles to 5.58 parts by weight and the used amount of the dicalcium phosphate anhydrous particles (C1) to 19.3 parts by weight and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7.

Example 38

A dentinal hypersensitivity inhibitor was prepared in the same manner as in Example 25 except for adjusting the used amount of the disodium hydrogen phosphate (B) particles to 5.36 parts by weight, using 17.1 parts by weight of dicalcium phosphate dihydrate particles (C) (average particle diameter=1.2 μm) instead of using 13.5 parts by weight of the dicalcium phosphate anhydrous particles (C1) and preparing the rest with purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7. Here, the above-mentioned dicalcium phosphate dihydrate particles (C) (average particle diameter=1.2 μm) were obtained by the same method as that used for preparing the dicalcium phosphate anhydrous particles (C1) in Example 25 using commercially available dicalcium phosphate dihydrate particles (produced by Wako Pure Chemical Industries, Ltd., average particle diameter=19 μm).

Example 39

A dentinal hypersensitivity inhibitor was prepared in the same manner as in Example 25 except for adjusting the used amount of the disodium hydrogen phosphate (B) particles to 5.98 parts by weight, using 23.3 parts by weight of monocalcium phosphate anhydrous particles (C) (average particle diameter=1.1 μm) instead of using 13.5 parts by weight of the dicalcium phosphate anhydrous particles (C1) and preparing the rest with purified water in Example 25, and then measurement of an alkali metal ion concentration, morphological evaluation, and dentin penetration inhibition ratio evaluation were performed. The composition of the dentinal hypersensitivity inhibitor used is summarized in Table 5, and the evaluation results obtained are summarized in Table 7. Here, the above-mentioned monocalcium phosphate anhydrous particles (C) (average particle diameter=1.1 μm) were obtained by the same method as that used for preparing the dicalcium phosphate anhydrous particles (C1) in Example 25 using commercially available monocalcium phosphate anhydrous particles (produced by Wako Pure Chemical Industries, Ltd., average particle diameter=18 μm).

Example 40

A dentinal hypersensitivity inhibitor was prepared in the same manner as in Example 25 except for adjusting the used amount of the disodium hydrogen phosphate (B) particles to 6.74 parts by weight, using 30.9 parts by weight of tricalcium phosphate particles (C) (average particle diameter=3.2 μm) instead of using 13.5 parts by weight of the dicalcium phosphate anhydrous particles (C1) and preparing the rest with purified water in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7. Here, "a-TCP-B (average particle diameter=3.2 μm)" produced by Taihei Chemical Industrial Co., Ltd. was used as received as the above-mentioned tricalcium phosphate particles (C) (average particle diameter=3.2 μm).

Example 41

A dentinal hypersensitivity inhibitor was prepared in the same manner as in Example 25 except for using 5 parts by weight of sodium dihydrogen phosphate (B) particles instead of using 5 parts by weight the disodium hydrogen phosphate (B) particles in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 42

A dentinal hypersensitivity inhibitor was prepared in the same manner as in Example 25 except for preparing it by adding 5 parts by weight of sodium dihydrogen phosphate (B) particles to the paste in liquid form instead of by adding 5 parts by weight of the disodium hydrogen phosphate (B) particles to the powder agent in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 43

A dentinal hypersensitivity inhibitor was prepared in the same manner as in Example 25 except for failing to use the sodium fluoride (D) particles and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 44

A dentinal hypersensitivity inhibitor was prepared in the same manner as in Example 25 except for failing to use the silica particles (E) for the paste in liquid form and preparing the rest by using purified water in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 45

A dentinal hypersensitivity inhibitor was prepared in the same manner as in Example 25 except for preparing it by adding 2 parts by weight of the silica particles (E) to the powder agent instead of by adding to the paste in liquid form in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 46

A dentinal hypersensitivity inhibitor was prepared in the same manner as in Example 25 except for preparing it by adding 36.5 parts by weight of tetracalcium phosphate particles (A2) having an average particle diameter of 35.6 μm instead of by adding 36.5 parts by weight of the tetracalcium phosphate particles (A4) having an average particle diameter of 5.2 μm in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 47

A dentinal hypersensitivity inhibitor was prepared in the same manner as in Example 25 except for preparing it by adding 36.5 parts by weight of tetracalcium phosphate particles (A3) having an average particle diameter of 20.3 μm instead of by adding 36.5 parts by weight of the tetracalcium phosphate particles (A4) having an average particle diameter of 5.2 μm in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 48

A dentinal hypersensitivity inhibitor was prepared in the same manner as in Example 25 except for preparing it by adding 36.5 parts by weight of tetracalcium phosphate particles (A5) having an average particle diameter of 1.5 μm instead of by adding 36.5 parts by weight of the tetracalcium phosphate particles (A4) having an average particle diameter of 5.2 μm in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 49

A dentinal hypersensitivity inhibitor was prepared by mixing a nonaqueous paste prepared using 36.5 parts by weight of tetracalcium phosphate particles (A4), 0.21 parts by weight of sodium fluoride (D) particles, 2 parts by weight of silica particles (E), 6.29 parts by weight of glycerol and 5 parts by weight of propylene glycol with an aqueous paste prepared using 5 parts by weight of disodium hydrogen phosphate (B) particles, 13.5 parts by weight of dicalcium phosphate anhydrous particles (C1), 5 parts by weight of xylitol, 3 parts by weight of polyethylene glycol, 0.05 parts by weight of cetyl pyridinium chloride monohydrate, 2 parts by weight of silica particles (E) and prepared the rest by using purified water instead of preparing the powder agent and the paste in liquid form in Example 25, and measurement of an alkali metal ion concentration, morphological evaluation and dentin penetration inhibition ratio evaluation were performed. The composition of the dentinal hypersensitivity inhibitor used is summarized in Table 3, and the evaluation results obtained are summarized in Table 7.

Example 50

A powder agent was obtained by adding tetracalcium phosphate particles (A4), disodium hydrogen phosphate (B) particles, dicalcium phosphate anhydrous particles (C1), and sodium fluoride (D) particles in the same amounts as those in Example 25 together with 200 g of 10-mm zirconia balls into a 400-ml pulverization pot made of alumina ("Type A-3 HD Pot Mill" manufactured by Nikkato Corp.) and mixing them at a rotation speed of 200 rpm for 30 minutes instead of using Method 1 by which a powder agent was prepared by using a high-speed rotary mill. The method for preparing a powder agent in which it is obtained by performing mixing in such a way was named "Method 2". Subsequently, a dentinal hypersensitivity inhibitor was prepared in the same manner as in Example 25, and measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 51

A powder agent for a dentinal hypersensitivity inhibitor was obtained by adding tetracalcium phosphate particles (A4), disodium hydrogen phosphate (B) particles, dicalcium phosphate anhydrous particles (C1), and sodium fluoride (D) particles in the same amounts as those in Example 25 into a pestle and mortar machine (automatic mortar, "ANM-200" manufactured by AS ONE Corporation) and mixing them with a mortar at a rotation speed of 6 rpm and a pestle at 100 rpm for five hours instead of using Method 1 by which a powder agent was prepared by using a high-speed rotary mill. The method for preparing a powder agent in which it is obtained by performing mixing in such a way was named "Method 3". Subsequently, a dentinal hypersensitivity inhibitor was prepared in the same manner as in Example 25, and measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 52

A powder agent for a dentinal hypersensitivity inhibitor was obtained by adding tetracalcium phosphate particles (A4), disodium hydrogen phosphate (B) particles, dicalcium phosphate anhydrous particles (C1), and sodium fluoride (D) particles in the same amounts as those in Example 25 into a 400-ml pulverization pot made of alumina ("Type A-3 HD Pot Mill" manufactured by Nikkato Corp.) without addition of zirconia balls and mixing them at a rotation speed of 1500 rpm for 30 minutes instead of using Method 1 by which a powder agent was prepared by using a high-speed rotary mill. The method for preparing a powder agent in which it is obtained by performing mixing in such a way was named "Method 4". Subsequently, a dentinal hypersensitivity inhibitor was prepared in the same manner as in Example 25, and measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 53

A dentinal hypersensitivity inhibitor was prepared in the same manner as in Example 25 except for preparing it by adding 13.5 parts by weight of dicalcium phosphate anhydrous particles (C2) having an average particle diameter of 10.2 μm instead of by adding 13.5 parts by weight of the dicalcium phosphate anhydrous particles (C1) having an average particle diameter of 1.1 μm in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Example 54

A dentinal hypersensitivity inhibitor was prepared in the same manner as in Example 25 except for preparing it by adding 13.5 parts by weight of dicalcium phosphate anhydrous particles (C3) having an average particle diameter of 17.1 μm instead of by adding 13.5 parts by weight of the dicalcium phosphate anhydrous particles (C1) having an average particle diameter of 1.1 μm in Example 25, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

Comparative Example 6

A dentinal hypersensitivity inhibitor was prepared in the same manner as in Example 25 except for failing to use the disodium hydrogen phosphate (B) particles in Example 25 and preparing the rest by using purified water, and then measurement of an alkali metal ion concentration, morphological evaluation, and dentin penetration inhibition ratio evaluation were performed. The composition of the dentinal hypersensitivity inhibitor used is summarized in Table 6, and the evaluation results obtained are summarized in Table 7.

TABLE 5

| | | Example 25 | Example 26 | Example 27 | Example 28 | Example 29 | Example 30 | Example 31 | Example 32 |
|---|---|---|---|---|---|---|---|---|---|
| Powder agent | Tetracalcium phosphate particle (A) | 36.5 (A4) | 36.5 (A4) | 36.5 (A4) | 36.5 (A4) | 36.5 (A4) | 36.5 (A4) | 21.9 (A4) | 21.9 (A4) |
| | Disodium hydrogen phosphate (B) particle | 5 | — | 0.15 | 0.3 | 2.5 | 20 | 21 | 27 |
| | Sodium dihydrogen phosphate (B) particle | — | — | — | — | — | — | — | — |
| | Dicalcium phosphate anhydrous particle (C) | 13.5 (C1) | 13.5 (C1) | 13.5 (C1) | 13.5 (C1) | 13.5 (C1) | 13.5 (C1) | 8.1 (C1) | 8.1 (C1) |
| | Dicalcium phosphate dihydrate particle (C) | — | — | — | — | — | — | — | — |
| | Monocalcium phosphate anhydrous particle (C) | — | — | — | — | — | — | — | — |
| | Tricalcium phosphate particle (C) | — | — | — | — | — | — | — | — |
| | Sodium fluoride (D) particle | 0.21 | 0.21 | 0.21 | 0.21 | 0.21 | 0.21 | 0.21 | 0.21 |
| | Silica particle (E) | — | — | — | — | — | — | — | — |
| Paste in liquid form | Disodium hydrogen phosphate (B) particle | — | 5 | — | — | — | — | — | — |
| | Sodium dihydrogen phosphate (B) particle | — | — | — | — | — | — | — | — |
| | Silica particle (E) | 2 | 2 | 2 | 2 | 2 | 2 | 2 | 2 |
| | Cetyl pyridinium chloride | 0.05 | 0.05 | 0.05 | 0.05 | 0.05 | 0.05 | 0.05 | 0.05 |
| | Purified water | 42.74 | 42.74 | 47.59 | 47.44 | 45.24 | 27.74 | 46.74 | 40.74 |
| Total | | 100 | 100 | 100 | 100 | 100 | 100 | 100 | 100 |
| Mixing method of powder agent | | Method 1 | Method 1 | Method 1 | Method 1 | Method 1 | Method 1 | Method 1 | Method 1 |
| Average of alkali metal ion concentration (mg/L) | | 7.7 | 0.6 | 0.7 | 0.9 | 4.3 | 23.3 | 33.6 | 38.6 |
| Standard deviation of ion concentration ($\sigma$)/Average of ion concentration (d) | | 0.04 | 0.05 | 0.05 | 0.04 | 0.05 | 0.06 | 0.07 | 0.09 |
| Blended amount of (B) to 100 parts by weight of (A) (parts by weight/parts by weight) | | 13.7 | 13.7 | 0.4 | 0.8 | 6.8 | 54.8 | 95.9 | 123.3 |
| Blended amount of (B) to 100 parts by weight of the sum total of (A) and (C) (parts by weight/parts by weight) | | 10 | 10 | 0.3 | 0.6 | 5 | 40 | 70 | 90 |
| Mixing ratio (A/C) (mol/mol) | | 1 | 1 | 1 | 1 | 1 | 1 | 1 | 1 |

| | | Example 33 | Example 34 | Example 35 | Example 36 | Example 37 | Example 38 | Example 39 |
|---|---|---|---|---|---|---|---|---|
| Powder agent | Tetracalcium phosphate particle (A) | 5.5 (A4) | 7.5 (A4) | 15 (A4) | 50 (A4) | 36.5 (A4) | 36.5 (A4) | 36.5 (A4) |
| | Disodium hydrogen phosphate (B) particle | 0.75 | 1.03 | 2.06 | 6.86 | 5.58 | 5.36 | 5.98 |
| | Sodium dihydrogen phosphate (B) particle | — | — | — | — | — | — | — |
| | Dicalcium phosphate anhydrous particle (C) | 2 (C1) | 2.8 (C1) | 5.6 (C1) | 18.6 (C1) | 19.3 (C1) | — | — |
| | Dicalcium phosphate dihydrate particle (C) | — | — | — | — | — | 17.1 | — |
| | Monocalcium phosphate anhydrous particle (C) | — | — | — | — | — | — | 23.3 |
| | Tricalcium phosphate particle (C) | — | — | — | — | — | — | — |

TABLE 5-continued

|  |  |  |  |  |  |  |  |  |
|---|---|---|---|---|---|---|---|---|
|  | Sodium fluoride (D) particle | 0.21 | 0.21 | 0.21 | 0.21 | 0.21 | 0.21 | 0.21 |
|  | Silica particle (E) | — | — | — | — | — | — | — |
| Paste in liquid form | Disodium hydrogen phosphate (B) particle | — | — | — | — | — | — | — |
|  | Sodium dihydrogen phosphate (B) particle | — | — | — | — | — | — | — |
|  | Silica particle (E) | 2 | 2 | 2 | 2 | 2 | 2 | 2 |
|  | Cetyl pyridinium chloride | 0.05 | 0.05 | 0.05 | 0.05 | 0.05 | 0.05 | 0.05 |
|  | Purified water | 89.49 | 86.41 | 75.08 | 22.28 | 36.36 | 38.78 | 31.96 |
| Total |  | 100 | 100 | 100 | 100 | 100 | 100 | 100 |
| Mixing method of powder agent |  | Method 1 | Method 1 | Method 1 | Method 1 | Method 1 | Method 1 | Method 1 |
| Average of alkali metal ion concentration (mg/L) |  | 10.5 | 9.6 | 8.4 | 7.6 | 7.7 | 7.7 | 7.6 |
| Standard deviation of ion concentration ($\sigma$)/Average of ion concentration (d) |  | 0.04 | 0.04 | 0.05 | 0.04 | 0.04 | 0.04 | 0.04 |
| Blended amount of (B) to 100 parts by weight of (A) (parts by weight/parts by weight) |  | 13.6 | 13.7 | 13.7 | 13.7 | 15.3 | 14.7 | 16.4 |
| Blended amount of (B) to 100 parts by weight of the sum total of (A) and (C) (parts by weight/parts by weight) |  | 10 | 10 | 10 | 10 | 10 | 10 | 10 |
| Mixing ratio (A/C) (mol/mol) |  | 1 | 1 | 1 | 1 | 0.7 | 1 | 1 |

Tetracalcium phosphate particles (A4): average particle diameter = 5.2 μm
Dicalcium phosphate anhydrous particle (C1): average particle diameter = 1.1 μm
Dicalcium phosphate dihydrate particle (C): average particle diameter = 1.2 μm
Monocalcium phosphate anhydrous particle (C): average particle diameter = 1.1 μm

TABLE 6

|  |  | Example 40 | Example 41 | Example 42 | Example 43 | Example 44 | Example 45 | Example 46 | Example 47 |
|---|---|---|---|---|---|---|---|---|---|
| Powder agent | Tetracalcium phosphate particle (A) | 36.5 (A4) | 36.5 (A4) | 36.5 (A4) | 36.5 (A4) | 36.5 (A4) | 36.5 (A4) | 36.5 (A2) | 36.5 (A3) |
|  | Disodium hydrogen phosphate (B) particle | 6.74 | — | — | 5 | 5 | 5 | 5 | 5 |
|  | Sodium dihydrogen phosphate (B) particle | — | 5 | — | — | — | — | — | — |
|  | Dicalcium phosphate anhydrous particle (C) | — | 13.5 (C1) | 13.5 (C1) | 13.5 (C1) | 13.5 (C1) | 13.5 (C1) | 13.5 (C1) | 13.5 (C1) |
|  | Dicalcium phosphate dihydrate particle (C) | — | — | — | — | — | — | — | — |
|  | Monocalcium phosphate anhydrous particle (C) | — | — | — | — | — | — | — | — |
|  | Tricalcium phosphate particle (C) | 30.9 | — | — | — | — | — | — | — |
|  | Sodium fluoride (D) particle | 0.21 | 0.21 | 0.21 | — | 0.21 | 0.21 | 0.21 | 0.21 |
|  | Silica particle (E) | — | — | — | — | — | 2 | — | — |
| Paste in liquid form | Disodium hydrogen phosphate (B) particle | — | — | — | — | — | — | — | — |
|  | Sodium dihydrogen phosphate (B) particle | — | — | 5 | — | — | — | — | — |
|  | Silica particle (E) | 2 | 2 | 2 | 2 | — | — | 2 | 2 |
|  | Cetyl pyridinium chloride | 0.05 | 0.05 | 0.05 | 0.05 | 0.05 | 0.05 | 0.05 | 0.05 |
|  | Purified water | 23.6 | 42.74 | 42.74 | 42.95 | 44.74 | 42.74 | 42.74 | 42.74 |
| Total |  | 100 | 100 | 100 | 100 | 100 | 100 | 100 | 100 |
| Mixing method of powder agent |  | Method 1 | Method 1 | Method 1 | Method 1 | Method 1 | Method 1 | Method 1 | Method 1 |
| Average of alkali metal ion concentration (mg/L) |  | 7.6 | 4.8 | 0.6 | 7.3 | 7.7 | 7.5 | 7.7 | 7.7 |
| Standard deviation of ion concentration ($\sigma$)/Average of ion concentration (d) |  | 0.04 | 0.04 | 0.05 | 0.04 | 0.04 | 0.04 | 0.04 | 0.04 |
| Blended amount of (B) to 100 parts by weight of (A) (parts by weight/parts by weight) |  | 18.5 | 13.7 | 13.7 | 13.7 | 13.7 | 13.7 | 13.7 | 13.7 |
| Blended amount of (B) to 100 parts by weight of the sum total of (A) and (C) (parts by weight/parts by weight) |  | 10 | 10 | 10 | 10 | 10 | 10 | 10 | 10 |
| Mixing ratio (A/C) (mol/mol) |  | 1 | 1 | 1 | 1 | 1 | 1 | 1 | 1 |

TABLE 6-continued

|  |  | Example 48 | Example 50 | Example 51 | Example 52 | Example 53 | Example 54 | Comparative Example 6 |
|---|---|---|---|---|---|---|---|---|
| Powder agent | Tetracalcium phosphate particle (A) | 36.5 (A5) | 36.5 (A4) | 36.5 (A4) | 36.5 (A4) | 36.5 (A4) | 36.5 (A4) | 36.5 (A4) |
|  | Disodium hydrogen phosphate (B) particle | 5 | 5 | 5 | 5 | 5 | 5 | — |
|  | Sodium dihydrogen phosphate (B) particle | — | — | — | — | — | — | — |
|  | Dicalcium phosphate anhydrous particle (C) | 13.5 (C1) | 13.5 (C1) | 13.5 (C1) | 13.5 (C1) | 13.5 (C2) | 13.5 (C3) | 13.5 (C1) |
|  | Dicalcium phosphate dihydrate particle (C) | — | — | — | — | — | — | — |
|  | Monocalcium phosphate anhydrous particle (C) | — | — | — | — | — | — | — |
|  | Tricalcium phosphate particle (C) | — | — | — | — | — | — | — |
|  | Sodium fluoride (D) particle | 0.21 | 0.21 | 0.21 | 0.21 | 0.21 | 0.21 | 0.21 |
|  | Silica particle (E) | — | — | — | — | — | — | — |
| Paste in liquid form | Disodium hydrogen phosphate (B) particle | — | — | — | — | — | — | — |
|  | Sodium dihydrogen phosphate (B) particle | — | — | — | — | — | — | — |
|  | Silica particle (E) | 2 | 2 | 2 | 2 | 2 | 2 | 2 |
|  | Cetyl pyridinium chloride | 0.05 | 0.05 | 0.05 | 0.05 | 0.05 | 0.05 | 0.05 |
|  | Purified water | 42.74 | 42.74 | 42.74 | 42.74 | 42.74 | 42.74 | 47.74 |
| Total |  | 100 | 100 | 100 | 100 | 100 | 100 | 100 |
| Mixing method of powder agent |  | Method 1 | Method 2 | Method 3 | Method 4 | Method 1 | Method 1 | Method 1 |
| Average of alkali metal ion concentration (mg/L) |  | 7.7 | 7.7 | 7.7 | 8.2 | 7.7 | 7.7 | 0.6 |
| Standard deviation of ion concentration ($\sigma$)/Average of ion concentration (d) |  | 0.08 | 0.02 | 0.01 | 0.54 | 0.04 | 0.04 | 0.04 |
| Blended amount of (B) to 100 parts by weight of (A) (parts by weight/parts by weight) |  | 13.7 | 13.7 | 13.7 | 13.7 | 13.7 | 13.7 | 0 |
| Blended amount of (B) to 100 parts by weight of the sum total of (A) and (C) (parts by weight/parts by weight) |  | 10 | 10 | 10 | 10 | 10 | 10 | 0 |
| Mixing ratio (A/C) (mol/mol) |  | 1 | 1 | 1 | 1 | 1 | 1 | 1 |

Tetracalcium phosphate particle (A2): average particle diameter = 35.6 μm
Tetracalcium phosphate particle (A3): average particle diameter = 20.3 μm
Tetracalcium phosphate particles (A4): average particle diameter = 5.2 μm
Tetracalcium phosphate particle (A5): average particle diameter = 1.5 μm
Dicalcium phosphate anhydrous particle (C1): average particle diameter = 1.1 μm
Dicalcium phosphate anhydrous particle (C2): average particle diameter = 10.2 μm (produced by J. T. Baker)
Dicalcium phosphate anhydrous particle (C3): average particle diameter = 17.1 μm (produced by Taihei Chemical Industrial Co., Ltd.)
Tricalcium phosphate particle (C): average particle diameter = 3.2 μm (produced by Taihei Chemical Industrial Co., Ltd.)

TABLE 7

|  | Penetration inhibition ratio (%) | Dentinal tubule closing depth (μm) |
|---|---|---|
| Example 25 | 92 | 15 |
| Example 26 | 90 | 14 |
| Example 27 | 37 | 10 |
| Example 28 | 52 | 11 |
| Example 29 | 86 | 12 |
| Example 30 | 82 | 10 |
| Example 31 | 64 | 12 |
| Example 32 | 31 | 11 |
| Example 33 | 27 | 4 |
| Example 34 | 39 | 7 |
| Example 35 | 68 | 10 |
| Example 36 | 82 | 3 |
| Example 37 | 84 | 12 |
| Example 38 | 91 | 14 |
| Example 39 | 85 | 11 |
| Example 40 | 78 | 9 |
| Example 41 | 91 | 14 |
| Example 42 | 88 | 14 |
| Example 43 | 86 | 12 |
| Example 44 | 88 | 12 |
| Example 45 | 90 | 13 |
| Example 46 | 51 | 4 |
| Example 47 | 78 | 6 |
| Example 48 | 66 | 13 |
| Example 49 | 81 | 14 |
| Example 50 | 99 | 14 |
| Example 51 | 100 | 15 |
| Example 52 | 54 | 13 |
| Example 53 | 52 | 6 |
| Example 54 | 42 | 4 |
| Comparative Example 6 | 22 | 10 |

EXPLANATION OF SYMBOLS

1 Dense HAp layer
2 Untreated portion
3 Dentinal tubule closed by HAp
4 Untreated portion
5 Mineralization(Dentinal Tubule closure)-treated portion

The invention claimed is:

1. A method for inhibiting dentinal hypersensitivity, the method comprising:
   closing at least one dentinal tubule on a dentin surface by rubbing the dentin surface with a dentinal hypersensitivity inhibitor,
   wherein the dentinal hypersensitivity inhibitor comprises at least one tetracalcium phosphate particle (A), an alkali metal salt of phosphoric acid (B), and at least one acidic calcium phosphate particle (C),
   wherein the at least one tetracalcium phosphate particle (A) has an average particle diameter of 0.5 to 30 μm,
   wherein the at least one acidic calcium phosphate particle (C) has an average particle diameter of 0.1 to 7 μm,
   wherein the dentinal hypersensitivity inhibitor comprises a blended amount of the at least one tetracalcium phosphate particle (A) of 15 to 55 parts by weight relative to 100 parts by weight of a whole amount of the dentinal hypersensitivity inhibitor and a blended amount of the alkali metal salt of phosphoric acid (B) of 6.8 to 54.8 parts by weight relative to 100 parts by weight of the at least one tetracalcium phosphate particle (A), and
   wherein a blending ratio of (A/C) of the at least one tetracalcium phosphate particle (A) to the at least one acidic calcium phosphate particle (C) is from 40/60 to 60/40 in a molar ratio.

2. The method of claim 1, wherein the alkali metal salt of phosphoric acid (B) is at least one selected from the group consisting of disodium hydrogen phosphate and sodium dihydrogen phosphate.

3. The method of claim 1, wherein the acidic calcium phosphate particle (C) is at least one member selected from the group consisting of a dicalcium phosphate anhydrous [$CaHPO_4$] particle, a monocalcium phosphate anhydrous [$Ca(H_2PO_4)_2$] particle, a tricalcium phosphate [$Ca_3(PO_4)_2$] particle, an amorphous calcium phosphate [$Ca_3(PO_4)_2.xH_2O$] particle, a calcium dihydrogen pyrophosphate [$CaH_2P_2O_7$] particle, a dicalcium phosphate dihydrate [$CaHPO_4.2H_2O$] particle, and a monocalcium phosphate monohydrate [$Ca(H_2PO_4)_2.H_2O$] particle.

4. The method of claim 1, wherein the dentinal hypersensitivity inhibitor further comprises a fluorine compound (D).

5. The method of claim 4, wherein the fluorine compound (D) is sodium fluoride.

6. The method of claim 1, wherein an average particle diameter of the alkali metal salt of phosphoric acid (B) is 0.5 to 20 μm.

7. The method of claim 1, wherein the dentinal hypersensitivity inhibitor further comprises at least one particle (E) of 0.002 to 2 μm in average particle diameter.

8. The method of claim 7, wherein the at least one particle (E) comprises silica or at least one metal oxide.

9. The method of claim 1, wherein when a suspension is prepared by adding 0.05 g of the dentinal hypersensitivity inhibitor into 200 g of pure water of 25° C., a free alkali metal ion concentration of the suspension at a time of 10 minutes after the adding is 0.2 to 100 mg/L.

* * * * *